United States Patent
Werner et al.

(10) Patent No.: US 10,259,822 B2
(45) Date of Patent: Apr. 16, 2019

(54) METHOD FOR THE PREPARATION OF COMPOUNDS HAVING A 16-OXABICYCLO[10.3.1]PENTADECENE SCAFFOLD AND THE SUBSEQUENT PRODUCTS THEREOF

(71) Applicant: BASF SE, Ludwigshafen am Rhein (DE)

(72) Inventors: Albert Werner, Bishop, TX (US); Miriam Bru Roig, Heidelberg (DE); Joaquim Henrique Teles, Waldsee (DE); Stefan Rüdenauer, Weinheim (DE); Stephan Maurer, Neustadt-Gimmeldingen (DE); Manuel Danz, Plankstadt (DE)

(73) Assignee: BASF SE (DE)

( * ) Notice: Subject to any disclaimer, the term of this patent is extended or adjusted under 35 U.S.C. 154(b) by 0 days.

(21) Appl. No.: 15/777,931

(22) PCT Filed: Nov. 22, 2016

(86) PCT No.: PCT/EP2016/078385
§ 371 (c)(1),
(2) Date: May 22, 2018

(87) PCT Pub. No.: WO2017/089327
PCT Pub. Date: Jun. 1, 2017

(65) Prior Publication Data
US 2018/0346478 A1 Dec. 6, 2018

(30) Foreign Application Priority Data
Nov. 23, 2015 (EP) .................................. 15195836

(51) Int. Cl.
C07C 45/60 (2006.01)
C07C 45/62 (2006.01)
C07D 493/06 (2006.01)

(52) U.S. Cl.
CPC ............ *C07D 493/06* (2013.01); *C07C 45/60* (2013.01); *C07C 45/62* (2013.01)

(58) Field of Classification Search
CPC ........ C07D 493/06; C07C 45/60; C07C 45/62
(Continued)

(56) References Cited

U.S. PATENT DOCUMENTS 3,777,483 A 12/1973 Lewis
3,778,483 A 12/1973 Firmenich S.A.
(Continued)

FOREIGN PATENT DOCUMENTS

CH 513791 A 10/1971
EP 0400509 A1 12/1990
(Continued)

OTHER PUBLICATIONS

Rohanna; Org lett 2009, 11, 493-495. (Year: 2009).*
(Continued)

*Primary Examiner* — Daniel R Carcanague
(74) *Attorney, Agent, or Firm* — Drinker Biddle & Reath LLP

(57) ABSTRACT

The present invention relates to a method for preparing compounds having a 16-oxabicyclo[10.3.1]pentadecene skeleton, specifically 14-methyl-16-oxabicyclo[10.3.1]pentadecenes, and conversion products thereof.

19 Claims, 1 Drawing Sheet

(58) Field of Classification Search
USPC .......................................................... 549/355
See application file for complete search history.

(56) References Cited

U.S. PATENT DOCUMENTS

| | | |
|---|---|---|
| 4,335,262 A | 6/1982 | Schulte-Elte et al. |
| 4,480,107 A | 10/1984 | Schulte-Elte et al. |
| 5,081,311 A | 1/1992 | Huellmann et al. |
| 9,951,756 B2 | 4/2018 | Wortmann et al. |
| 2016/0312149 A1 | 10/2016 | Vautravers et al. |
| 2016/0318860 A1 | 11/2016 | Vautravers et al. |
| 2016/0332944 A1 | 11/2016 | Rüdenauer et al. |
| 2017/0010024 A1 | 1/2017 | Wortmann et al. |
| 2017/0037020 A1 | 2/2017 | Rüdenauer et al. |
| 2017/0037022 A1 | 2/2017 | Stork et al. |
| 2017/0066705 A1 | 3/2017 | Hickmann et al. |
| 2017/0107166 A1 | 4/2017 | Limbach et al. |
| 2017/0107168 A1 | 4/2017 | Vautravers et al. |
| 2017/0183280 A1 | 6/2017 | Vautravers et al. |
| 2017/0197830 A1 | 7/2017 | Riedel et al. |
| 2017/0205151 A1 | 7/2017 | Wortmann et al. |
| 2017/0217869 A1 | 8/2017 | Limbach et al. |
| 2017/0246620 A1 | 8/2017 | Parvulescu et al. |
| 2017/0275225 A1 | 9/2017 | Riedel et al. |
| 2017/0283352 A1 | 10/2017 | Fenlon et al. |
| 2017/0292084 A1 | 10/2017 | Stork et al. |
| 2017/0320847 A1 | 11/2017 | Vautravers et al. |
| 2017/0355670 A1 | 12/2017 | Rüdenauer et al. |
| 2017/0362153 A1* | 12/2017 | Tanino .................... C07B 61/00 |
| 2017/0362532 A1 | 12/2017 | Pelzer et al. |
| 2018/0002266 A1 | 1/2018 | Bru Roig et al. |
| 2018/0023421 A1 | 1/2018 | Wortmann et al. |
| 2018/0036723 A1 | 2/2018 | Riedel et al. |
| 2018/0044313 A1 | 2/2018 | Rüdenauer et al. |
| 2018/0112929 A1 | 4/2018 | Wortmann et al. |
| 2018/0141888 A1* | 5/2018 | Rudenauer .............. C07C 45/30 |
| 2018/0170850 A1* | 6/2018 | Vautravers .............. C07C 45/64 |
| 2018/0171262 A1* | 6/2018 | Rudenauer .............. C07C 29/14 |
| 2018/0179136 A1* | 6/2018 | Bru Roig ................ C01B 15/01 |
| 2018/0208532 A1* | 7/2018 | Parvulescu ............. C07C 41/18 |
| 2018/0208533 A1* | 7/2018 | Rudenauer .............. C07C 41/18 |
| 2018/0208745 A1* | 7/2018 | Vautravers ........... C08K 5/0025 |
| 2018/0215694 A1* | 8/2018 | Riedel ................... C01B 15/023 |
| 2018/0215724 A1* | 8/2018 | Gordillo ............... C07D 307/46 |
| 2018/0230076 A1* | 8/2018 | Thrun ................... C11B 9/0038 |
| 2018/0230117 A1* | 8/2018 | Teles .................... C07D 301/12 |
| 2018/0237369 A1* | 8/2018 | Fenlon .................... C07C 41/01 |
| 2018/0244613 A1* | 8/2018 | Rudenauer .............. C07C 45/39 |
| 2018/0265443 A1* | 9/2018 | Vautravers .............. C07C 45/28 |
| 2018/0273458 A1* | 9/2018 | Strautmann ............ C07C 45/50 |

FOREIGN PATENT DOCUMENTS

| | | | |
|---|---|---|---|
| JP | 2002335991 A | 11/2002 | |
| JP | 2012046444 A | 3/2012 | |
| WO | WO-2015107017 A1 * | 7/2015 | ............ C11B 9/0038 |
| WO | WO-2017050713 A1 * | 3/2017 | ............ C07C 29/132 |
| WO | WO-2017060437 A1 * | 4/2017 | ............ C07C 45/28 |
| WO | WO-2018011386 A1 * | 1/2018 | ............ C07D 307/93 |

OTHER PUBLICATIONS

Fehr; Helvetica Chimica Acta 1983, 66, 2512-2518. (Year: 1983).*
Schulte-Elte; Helvetica Chimica Acta 1979, 62, 2673-2680. (Year: 1979).*
English Translation of International Preliminary Report on Patentability with Written Opinion for International Application No. PCT/EP2016/078385, dated Jun. 7, 2018.
International Search Report for PCT/EP2016/078385 dated Feb. 1, 2017.
Written Opinion of the International Searching Authority for PCT/EP2016/078385 dated Feb. 1, 2017.

* cited by examiner

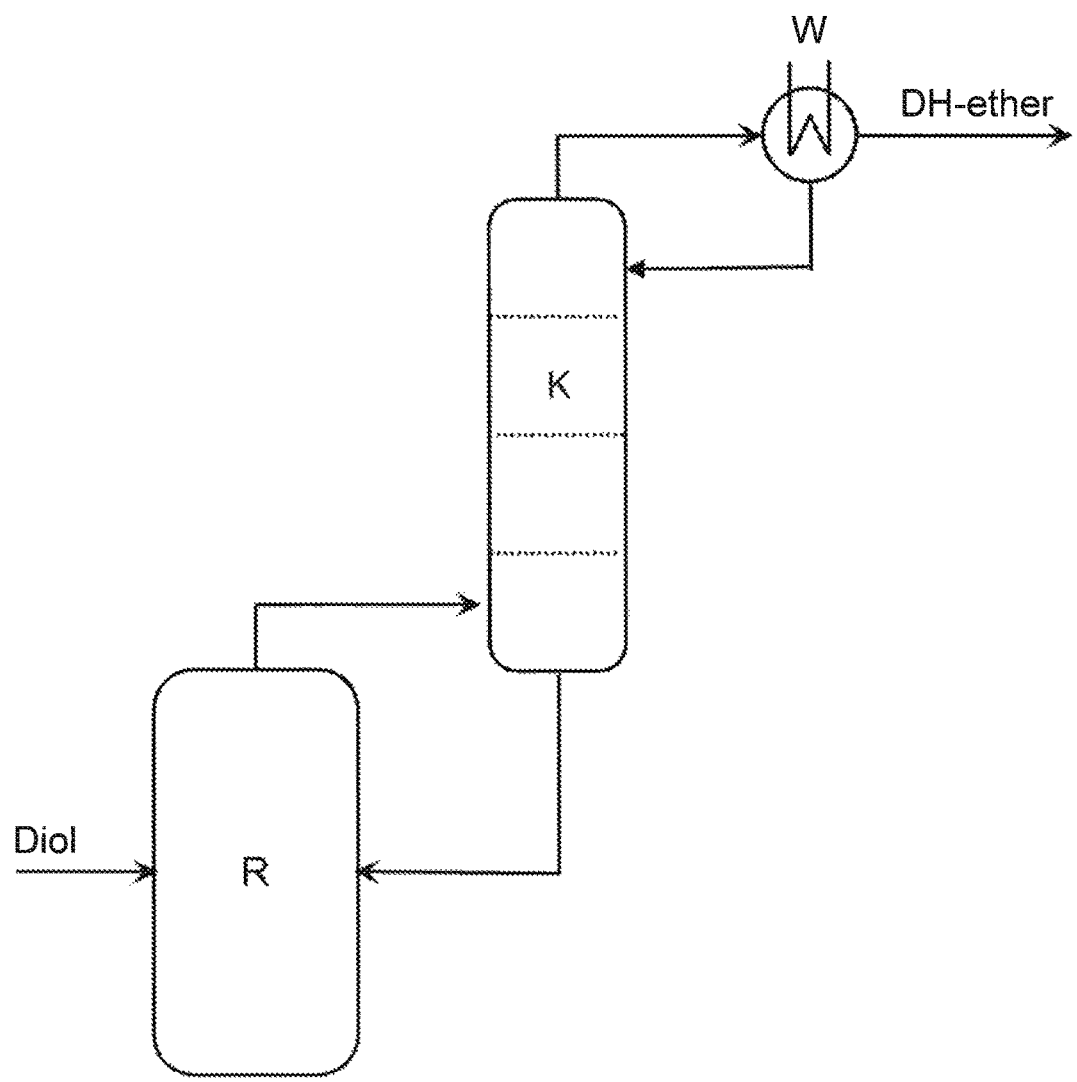

METHOD FOR THE PREPARATION OF COMPOUNDS HAVING A 16-OXABICYCLO[10.3.1]PENTADECENE SCAFFOLD AND THE SUBSEQUENT PRODUCTS THEREOF

CROSS-REFERENCE TO RELATED APPLICATIONS

This application is a national stage application (under 35 U.S.C. § 371) of PCT/EP2016/078385, filed Nov. 22, 2016, which claims benefit of European Application No. 15195836.0, filed Nov. 23, 2015, both of which are incorporated herein by reference in their entirety.

BACKGROUND OF THE INVENTION

The present invention relates to a method for preparing compounds having a 16-oxabicyclo[10.3.1]pentadecene skeleton, especially 14-methyl-16-oxabicyclo[10.3.1]pentadecenes, and conversion products thereof.

PRIOR ART

Makrocyclic ketones having 14- to 18-membered rings, for example, cyclopentadecanone (exaltone), 3-methylcyclopentadecanone (muscone) and 3-methylcyclopentadecenone (dehydromuscone or Muscenone®), are desirable fragrances or aroma substances, whose synthetic preparation was and is the subject of extensive investigations. In particular, the non-naturally occurring mixture of 3-methylcyclopentadec-4-en-1-one and 3-methylcyclopentadec-5-en-1-one is of particular interest owing to its olfactory properties. This mixture of 3-methylcyclopentadec-4-en-1-one and 3-methylcyclopentadec-5-en-1-one is referred to below as "dehydromuscone". The formula (A) below, in which the symbol ⟿ is in one case a single bond and in one case a double bond, shows dehydromuscone without consideration of positional and double bond isomers. The formulae (A') and (A") show the two double bond isomers without consideration of the cis-trans isomers of the double bonds.

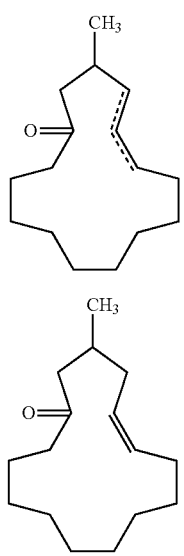

(A)

(A')

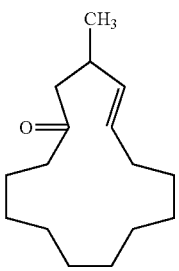

(A")

In the context of the invention, structure (A) includes the pure compound (A'), the pure compound (A") and any mixtures of (A') and (A"), where the double bonds can each have either a cis or trans geometry.

The synthesis of dehydromuscone is described, inter alia, in the following documents: U.S. Pat. No. 3,778,483; U.S. Pat. No. 4,480,107 and CH 513791.

The isomers of 14-methyl-16-oxabicyclo[10.3.1]pentadecene (D) are important inter-mediates in the preparation of dehydromuscone (A) and muscone. For instance, a three-stage synthesis of dehydromuscone (A) may start from 3-methylcyclopentadecane-1,5-dione (B) and may comprise the following steps:

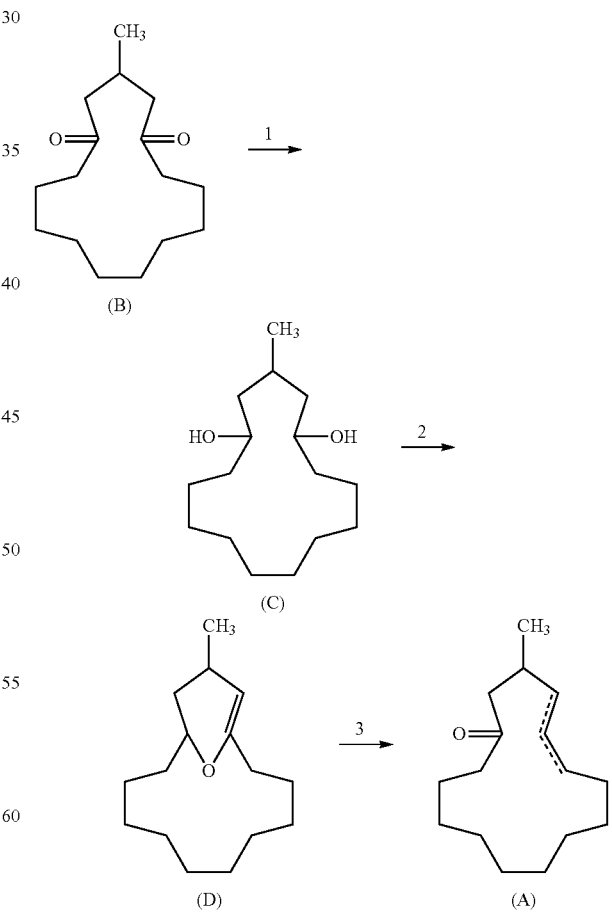

1. Reduction of 3-methylcyclopentadecane-1,5-dione (B) to 3-methylcyclopentadecane-1,5-diol (C).

2. Catalytic dehydrogenation and dehydration of the 3-methylcyclopentadecane-1,5-diol (C) to 14-methyl-16-oxabicyclo[10.3.1]pentadecene (D).
3. Conversion of the 14-Methyl-16-oxabicyclo[10.3.1]pentadecene (D) to dehydromuscone (A).

In stage 2), the 3-methylcyclopentadecane-1,5-dione (B) and 14-methyl-16-oxabicyclo[10.3.1]hexadecane (E) may occur as by-products. Furthermore, during the conversion of the 3-methylcyclopentadecane-1,5-diol (C) to the 14-methyl-16-oxabicyclo[10.3.1]pentadecene (D), 3-methylcyclopentadecan-5-ol-1-one (F) may be formed as intermediate:

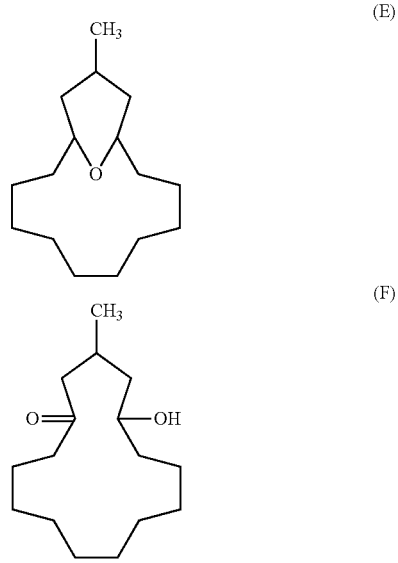

U.S. Pat. No. 4,335,262 describes, inter alia, the preparation of dehydromuscone (A) via dehydrogenation and dehydration of 3-methylcyclopentadecane-1,5-diol (C) to give 14-methyl-16-oxabicyclo[10.3.1]pentadecene (D) using Raney copper in batch mode (Example 4 of U.S. Pat. No. 4,335,262). In this case, 14-methyl-16-oxabicyclo[10.3.1]pentadecene is separated from the reaction mixture directly by distillation. Subsequently, 14-methyl-16-oxabicyclo[10.3.1]pentadecene can be subjected to a reaction with phosphoric acid in toluene to obtain the dehydromuscone (A) (Example 5 of U.S. Pat. No. 4,335,262).

A disadvantage of this method, however, is the low selectivity for dehydromuscone (A), since not inconsiderable amounts of the saturated ether (E) are obtained, inter alia, which reduce both the yield and the purity of the target product. Furthermore, the high viscosity of the reaction mixture makes the technical implementation of this method more difficult.

The object of the present invention is to provide an improved method for preparing 16-oxabicyclo[10.3.1]pentadecenes, in which the ring carbon atom 14 is unsubstituted or bears a $C_1$-$C_4$-alkyl residue. The synthesis should proceed in this case from the corresponding cyclopentadecane-1,5-dials. In particular, the object of the invention is to provide an improved method for preparing 14-methyl-16-oxabicyclo[10.3.1]pentadec-12-ene, starting from 3-methylcyclopentadecane-1,5-diol. Here, the 16-oxabicyclo[10.3.1]-pentadecenes and especially 14-methyl-16-oxabicyclo[10.3.1]pentadecene should be attained with a high conversion in good yield and purity.

It has now been found that this object is achieved by converting the corresponding cyclopentadecane-1,5-diol to the unsubstituted or $C_1$-$C_4$-alkyl-substituted 16-oxabicyclo-[10.3.1]pentadecene over a dehydrogenating and dehydrating catalyst and additionally in the presence of a high-boiling solvent.

Specifically, it has been found that the unsubstituted or $C_1$-$C_4$-alkyl-substituted 16-oxabicyclo[10.3.1]pentadecenes, such as 14-methyl-16-oxabicyclo[10.3.1]pentadecene, further react to the undesired saturated ether during an excessively long residence time in the reaction zone in contact with the catalyst and the hydrogen formed during the reaction. By addition of a high-boiling solvent according to the invention, it is possible to make the cyclopentadecane-1,5-diol starting material, e.g. 3-methylcyclopentadecane-1,5-diol, and the catalyst remain in the reaction zone, while the residence time of the unsubstituted or $C_1$-$C_4$-alkyl-substituted 16-oxabicyclo[10.3.1]pentadecene in the reaction zone can be minimized. In this manner, it is possible to achieve high yields on the one hand based on the cyclopentadecane-1,5-dial used, and at the same time improved yield and purity of the unsubstituted or $C_1$-$C_4$-alkyl-substituted 16-oxabicyclo-[10.3.1]pentadecene. In addition, the mixing of the reaction mixture in the reaction zone can be improved by the addition of a high-boiling solvent according to the invention (or the viscosity of the reaction mixture can be reduced).

In particular, an apparatus is used to carry out the method according to the invention which apparatus comprises a reaction zone and a distillation zone linked thereto. In particular, after the start of the reaction in the reaction zone, a portion of the unsubstituted or $C_1$-$C_4$-alkyl-substituted 16-oxabicyclo[10.3.1]pentadecene is in the distillation zone, even if no unsubstituted or $C_1$-$C_4$-alkyl-substituted 16-oxabicyclo[10.3.1]pentadecene is withdrawn therefrom. Also by means of this procedure, the residence time of the unsubstituted or $C_1$-$C_4$-alkyl-substituted 16-oxabicyclo[10.3.1]pentadecene in the reaction zone can be minimized and therefore its thermal stress.

The method according to the invention especially serves for preparing 14-methyl-16-oxabicyclo[10.3.1]pentadec-12-ene, starting from 3-methylcyclopentadecane-1,5-diol. In this specific embodiment, after the start of the reaction in the reaction zone, a portion of the 14-methyl-16-oxabicyclo[10.3.1]pentadecene is in the distillation zone, even if no 14-methyl-16-oxabicyclo[10.3.1]pentadecene is withdrawn therefrom.

SUMMARY OF THE INVENTION

The invention relates to a method for preparing compounds of the general formula (I)

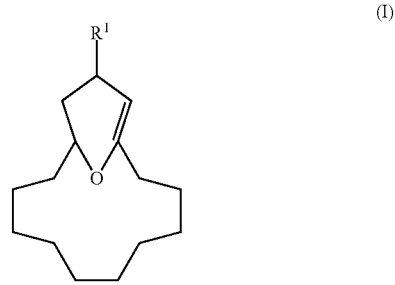

where $R^1$ is hydrogen or $C_1$-$C_4$-alkyl,
and conversion products thereof, wherein
a) a starting material is provided comprising a compound of the general formula (II)

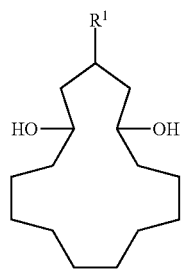

(II)

b) the starting material provided in step a) is subjected in a reaction zone to a reaction at a temperature in a range from 100 to 240° C. and a pressure in a range from 0.1 to 150 mbar in the presence of a heterogeneous catalyst and a solvent or a solvent mixture having a vapor pressure between $10^{-5}$ to 100 mbar at 180° C., and
c) the compound of formula (I) is separated from the reaction mixture by distillation.

The invention further relates to a method in which in addition
d) the compounds of the general formula (I) are subjected to a reaction to obtain at least one compound of the general formula (IV)

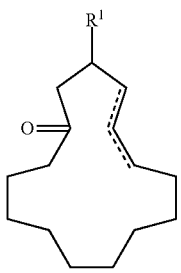

(IV)

where the symbol $=\!=\!=$ is in one case a single bond and in one case a double bond and $R^1$ is hydrogen or $C_1$-$C_4$-alkyl.

The invention further relates to a method in which in addition
e) the compounds of the general formula (IV) are subjected to a hydrogenation to obtain the compound of the general formula (V)

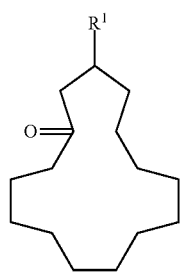

(V)

where $R^1$ is hydrogen or $C_1$-$C_4$-alkyl.

EMBODIMENTS OF THE INVENTION

The method according to the invention comprises the following embodiments:

1. A method for preparing compounds of the general formula (I)

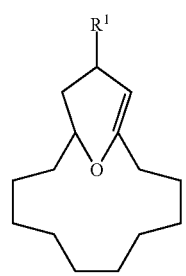

(I)

where $R^1$ is hydrogen or $C_1$-$C_4$-alkyl,
and conversion products thereof,
wherein
a) a starting material is provided comprising a compound of the general formula (II)

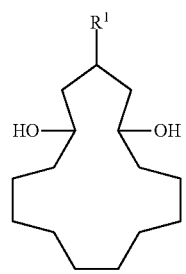

(II)

b) the starting material provided in step a) is subjected in a reaction zone to a reaction at a temperature in a range from 100 to 240° C. and a pressure in a range from 0.1 to 150 mbar in the presence of a heterogeneous catalyst and a solvent or a solvent mixture having a vapor pressure in the range from $10^{-5}$ to 100 mbar at 180° C., and
c) the compound of formula (I) is separated from the reaction mixture by distillation.

2. The method according to embodiment 1, wherein $R^1$ is hydrogen or methyl, particularly methyl.

3. The method according to embodiment 1 or 2, wherein the reaction in step b) comprises a first phase, during which the fraction not comprising any of the compound of formula (I) is separated from the reaction mixture by distillation.

4. The method according to any of the preceding embodiments, wherein the separation of a fraction comprising the compound of formula (I) from the reaction zone by distillation in step c) is carried out in a phasewise manner or continuously.

5. The method according to any of embodiments 1 to 4, wherein the vapor pressure of the solvent used in step b) is less than the vapor pressure of dial (I).

6. The method according to any of embodiments 1 to 4, wherein the vapor pressure of the solvent used in step b) is between the vapor pressure of compound (I) and the vapor pressure of compound (II).
7. The method according to any of embodiments 1 to 4, wherein the vapor pressure of the solvent used in step b) is between the vapor pressure of compound (I) and the vapor pressure of compound (III)

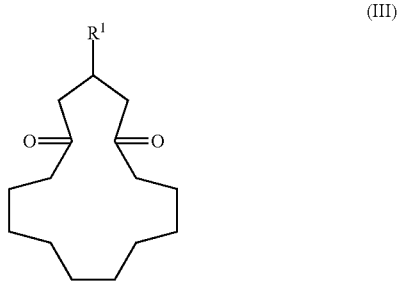

(III)

where $R^1$ is hydrogen or $C_1$-$C_4$-alkyl,
8. The method according to any of the preceding embodiments, wherein the solvent used in step b) is selected from
aliphatic, cycloaliphatic and aromatic hydrocarbons,
aliphatic, cycloaliphatic and aromatic monohydric and polyhydric alcohols,
ether alcohols, polyether polyols and mono- and dialkyl ethers thereof, aromatic ethers and open-chain aliphatic ethers,
ketones,
esters,
mixtures thereof.
9. The method according to any of the preceding embodiments, wherein the solvent used in step b) is selected from
$C_{10}$-$C_{30}$-alkanes,
$C_6$-$C_{30}$-alkanols,
$C_2$-$C_{30}$-alkanediols,
polyalkylene glycols and mono- and dialkylethers thereof,
mixtures thereof.
10. The method according to any of embodiments 1 to 9, wherein the separation in step c) is effected by one-stage distillation.
11. The method according to embodiment 10 for preparing 14-methyl-16-oxabicyclo[10.3.1]pentadecene (I.1), wherein the compound of formula (I.1) is separated from the reaction mixture in step c) by one-stage distillation and the product separated comprises the following compounds, based in each case on the total weight of the separated product:
14-methyl-16-oxabicyclo[10.3.1]pentadecene (I.1): 75-95% by weight,
3-methylcyclopentadecane-1,5-diol (II.1): 0-5% by weight,
3-methylcyclopentadecane-1,5-dione (III.1): 1-10% by weight,
14-methyl-16-oxabicyclo[10.3.1]hexadecane (VI.1): 0-15% by weight.
12. The method according to any of embodiments 1 to 9, wherein the separation in step c) comprises a fractional distillation.
13. The method according to embodiment 12, wherein at least one distillation column, preferably a distillation column, having at least 10 theoretical plates is used for the separation by distillation of a fraction comprising the compound of formula (I) in step c).
14. The method according to embodiment 12 or 13, wherein in the distillation the ratio of stream separated to the stream recirculated into the column is in the range from 1:1 to 1:30, and especially in the range of 1:1 to 1:20.
15. The method according to any of embodiments 12 to 14 for preparing 14-methyl-16-oxabicyclo[10.3.1]pentadecene (I.1), wherein the compound of formula (I) is separated from the reaction mixture in step c) by fractional distillation and the product separated comprises the following compounds, based in each case on the total weight of the separated product:
14-methyl-16-oxabicyclo[10.3.1]pentadecene (I.1): 80-99% by weight,
3-methylcyclopentadecane-1,5-diol (II.1): 0-5% by weight,
3-methylcyclopentadecane-1,5-dione (III.1): 0 to 5% by weight, preferably 0 to 1% by weight,
14-methyl-16-oxabicyclo[10.3.1]hexadecane (VI.1): 0 to 15% by weight, preferably 0 to 10% by weight,
solvent: 0 to 5% by weight, preferably 0 to 1% by weight,
3-methylcyclopentadecan-5-ol-1-one (VII.1): 0-5% by weight.
16. The method according to any of the preceding embodiments, wherein the solvent content of the reaction mixture in step b) is always maintained at at least 20% by weight, preferably at least 30% by weight, in particular at least 50% by weight, based on the total weight of the reaction mixture in the reaction zone.
17. The method according to any of the preceding embodiments, wherein a copper-containing catalyst, preferably Raney copper, is used as catalyst in step b).
18. The method according to any of the preceding embodiments, wherein in addition
d) the compounds of the general formula (I) are subjected to a reaction to obtain at least one compound of the general formula (IV)

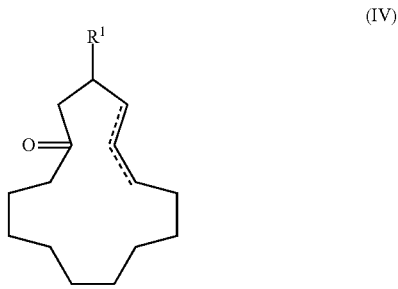

(IV)

where the symbol ═══ is in one case a single bond and in one case a double bond and $R^1$ is hydrogen or $C_1$-$C_4$-alkyl.
19. The method according to embodiment 18, wherein in addition
e) the compounds of the general formula (IV) are subjected to a hydrogenation to obtain the compound of the general formula (V)

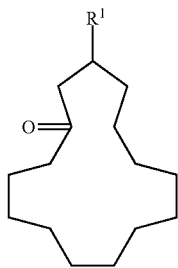

(V)

where $R^1$ is hydrogen or $C_1$-$C_4$-alkyl.

20. The method according to embodiment 18 or 19, wherein $R^1$ is hydrogen or methyl, particularly methyl.

DESCRIPTION OF THE INVENTION

The method according to the invention can be understood in principle as a reactive distillation but in which reaction zone and subsequent distillation zone are not necessarily integrally linked to each other. Thus, the catalyst and the cyclopentadecane-1,5,-diol used as reactant remain in the reaction zone (in the bottom), while the residence time of the product in the reaction zone is minimized. This is possible by the addition of a suitable solvent. In this manner, a high conversion of cyclopentadecane-1,5-diol (II) and at the same time improved yield and purity of the product of formula (I) is obtained.

The process according to the invention has the following advantages:

the method according to the invention enables a sufficient contact time of the cyclopentadecane-1,5-diol (II) with the catalyst and at the same time a low contact time of the product in the reaction zone.

the conditions in the separative distillation of compound (I) can then be specifically configured to be mild, if the vapor pressure of the solvent used in step b) is between the vapor pressure of compound (I) and the vapor pressure of compound (II). The vapor pressure of the solvent used in step b) is preferably between the vapor pressure of compound (I) and the vapor pressure of compound (III). Thus, lower temperatures and/or a weaker vacuum are required. In the specific embodiment of the invention for preparing 14-methyl-16-oxabicyclo[10.3.1]pentadecene (I.1) from 3-methylcyclopentadecane-1,5-diol (II.1), the vapor pressure of the solvent used in step b) is preferably between the vapor pressure of compound (I.1) and the vapor pressure of compound (II.1). The vapor pressure of the solvent used in step b) is then particularly preferably between the vapor pressure of compound (I.1) and the vapor pressure of compound (III.1).

by the use of solvents, the mixing of the reaction mixture in the bottom can also be improved.

the method according to the invention enables the use of a low amount of catalyst, based on the amount of cyclopentadecane-1,5-diol present in the reaction zone. This advantage is already apparent in a discontinuous mode of operation without replenishing converted cyclopentadecane-1,5-diol in the course of the reaction. This advantage is distinctly greater in a mode of operation in which further cyclopentadecane-1,5-dial is fed into the reaction zone in the course of the reaction. This applies especially to a continuous mode of operation.

the compounds of the general formula (I) and especially 14-methyl-16-oxabicyclo[10.3.1]pentadecene (I.1) can therefore be attained with high conversion in good yield and purity with the method according to the invention.

In the context of the present invention, $R^1$ is $C_1$-$C_4$-alkyl and is preferably methyl, ethyl, n-propyl, isopropyl or n-butyl.

In the compounds of formulae (I), (II), (III), (IV), (V), (VI) and (VII), $R^1$ is preferably hydrogen or methyl, particularly methyl.

In a preferred embodiment, the invention relates to a method for preparing compounds of the formula (I.1)

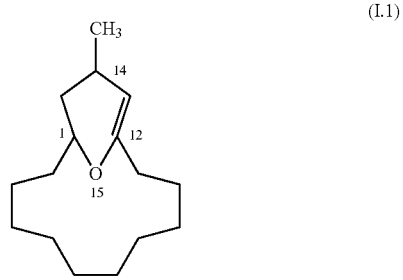 [SMILES: CC1C=C2CCCCCCCCCCC(C1)O2]

(I.1)

The compound of general formula (I.1) is referred to as 14-methyl-16-oxabicyclo[10.3.1]pentadec-12-ene. The specification of the position of the double bond is sometimes omitted below and a synonym of the term 14-methyl-16-oxabicyclo[10.3.1]pentadecene is used.

Unless exactly specified in the following, the general formulae (I) and (I.1) refer to E/Z mixtures of any composition and the pure conformational isomers. Furthermore, the general formulae (I) and (I.1) refer to all stereoisomers in pure form and also racemic and optically active mixtures of the compounds of formulae (I) and (I.1).

Unless exactly specified in the following, the general formula (II) refers to mixtures of the possible cis/trans isomers in any composition and also the pure constitutional isomers.

The starting material provided in step a) preferably comprises a compound of the general formula (II.1):

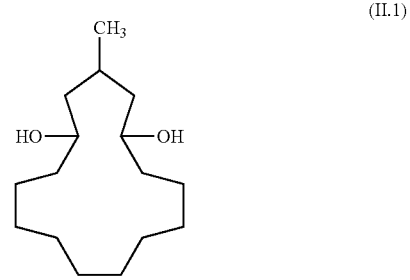

(II.1)

The compound of general formula (II.1) is referred to as 3-methylcyclopentadecane-1,5-diol.

In particular, an apparatus is used to carry out the method according to the invention which apparatus comprises a reaction zone and a distillation zone linked thereto. Specifically, after the start of the reaction in the reaction zone, a portion of the compound of formula (I) is in the distillation zone, even if no compound of formula (I) is (yet) withdrawn therefrom. This may occur, for example, at the beginning of the reaction or during the separation by distillation of the compound of formula (I) in a phasewise manner, e.g. if the content of compound (I) at the top of the column is too low. Also by means of this procedure, the residence time of the compound of formula (I) in the reaction zone can be minimized and therefore its thermal stress.

The method according to the invention especially serves for preparing 14-methyl-16-oxabicyclo[10.3.1]pentadec-12-ene (I.1), starting from 3-methylcyclopentadecane-1,5-diol (II.1). In this specific embodiment, after the start of the reaction in the reaction zone, a portion of the 14-methyl-16-oxabicyclo[10.3.1]pentadecene (I.1) is in the distillation zone, even if no 14-methyl-16-oxabicyclo[10.3.1]pentadecene (I.1) is withdrawn therefrom.

The method according to the invention can be carried out continuously, semi-continuously (semi-batch mode) or discontinuously (batch mode).

A continuous mode of operation is understood to mean that, apart from a start-up phase at the beginning of the reaction, the compound of the general formula (II) (especially 3-methylcyclopentadecane-1,5-diol (II.1)) is fed continuously to the reaction zone and the compound of the general formula (I) (especially 14-methyl-16-oxabicyclo-[10.3.1]pentadecene (I.1)) is separated continuously by distillation from the reaction mixture. In this case, the compound of general formula (II) is preferably fed in depending on the amount of compound of general formula (I) separated. The mixture in the reaction zone is then preferably essentially in the stationary state, i.e. the concentration of the compound of general formula (II) and the compound of the general formula (I) is essentially constant in the reaction mixture.

In the discontinuous mode of operation, a portion or the total amount of the compound of general formula (II) is fed to the reaction zone prior to the start of the reaction. As soon as a sufficient amount of the compound of the general formula (I) has formed, this is separated by distillation. Optionally, fresh compound (II) can be introduced into the reaction zone after decline of the content of compound (II) below a certain threshold in the reaction zone. This can be carried out both once and repeatedly.

A semi-continuous mode of operation is also possible, in which one of the steps, addition of the compound of the general formula (II) or separation of the compound of the general formula (I), is carried out continuously and the other in batch mode.

Step a):

The compounds of the general formula (II) and preparation thereof are known in principle. For instance, a compound of the general formula (III)

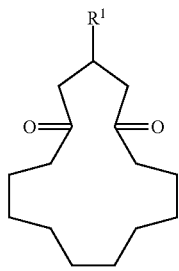

(III)

where $R^1$ is hydrogen or $C_1$-$C_4$-alkyl, can be subjected to a reaction with hydrogen in the presence of a hydrogenation catalyst.

To provide 3-methylcyclopentadecane-1,5-diol (II.1) as starting material in step a), the 3-methylcyclopentadecane-1,5-dione of formula (III.1)

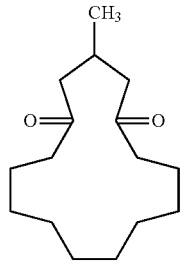

(III.1)

is preferably subjected to a reaction with hydrogen in the presence of a hydrogenation catalyst.

Suitable hydrogenation catalysts having a high selectivity for hydrogenation of both keto groups to alcohol groups are in principle the transition metal catalysts known to those skilled in the art for hydrogenation reactions. In general, the catalyst comprises at least one transition metal of groups 7, 8, 9, 10 and 11 of the IUPAC Periodic Table. Preferably, the catalyst has at least one transition metal from the group of Mn, Re, Fe, Ru, Co, Rh, Ir, Ni, Pd, Pt, Cu and Au. The catalyst particularly preferably has Ni. The hydrogenation catalysts consist of the transition metals mentioned as such or comprise the transition metals mentioned applied to a support, as precipitated catalysts, as Raney catalysts or as mixtures thereof.

Preference is given to using a Raney catalyst as hydrogenation catalyst. A suitable hydrogenation catalyst is Raney nickel.

The molar ratio of hydrogen to compound (III) is preferably 1000:1 to 1:1, more preferably 100:1 to 5:1.

The hydrogenation is preferably carried out at a temperature in the range of 10 to 250° C., particularly preferably 20 to 200° C.

The hydrogenation is preferably carried out in the liquid phase in the presence of a solvent.

The solvent used for the hydrogenation is preferably selected from water, aliphatic $C_1$- to $C_5$-alcohols, aliphatic $C_2$- to $C_6$-diols, ethers and mixtures thereof. Preferably, the solvent is selected from methanol, ethanol, n-propanol, isopropanol, n-butanol, sec-butanol, isobutanol and tert-butanol, ethylene glycol, propane-1,3-diol, butane-1,4-diol, pentane-1,5-diol, hexane-1,6-diol, tetrahydrofuran, 2-methyltetrahydrofuran, diethyl ether, methyl tert-butyl ether and mixtures thereof.

The reaction mixture obtained in the hydrogenation of the compound of formula (III), before use thereof as starting material in step a) of the method according to the invention, may be subjected to at least one work-up step. Suitable work-up steps are selected from:
separation of the solvent used in the hydrogenation,
separation of non-hydrogenated compound of formula (III),
separation of undesired by-products,
or a combination of at least two of the abovementioned measures.

Undesired by-products in the hydrogenation of 3-methylcyclopentadecane-1,5-dione (III) include the partially hydrogenated ketoalcohol (3-methylcyclopentadecan-5-ol-1-one) and also unsaturated compounds.

The reaction mixture from the hydrogenation of the compound of the general formula (III) is preferably subjected to a separation by distillation. In the simplest case, a distillation apparatus for one-stage (simple) distillation can be used for this distillation. Further suitable apparatuses for distillative separation of the reaction mixture from the hydrogenation of compound (III) comprise distillation columns such as tray columns, which may be equipped with bubble-caps, sieve plates, sieve trays, structured packings, random packings, valves, side draws, etc., evaporators such as thin film evaporators, falling film evaporators, forced circulation evaporators, Sambay evaporators etc., and combinations thereof.

The distillation columns may have separating internals, preferably selected from separating trays, stacked packings, e.g. sheet metal or fabric packings such as Sulzer Mellapak®, Sulzer BX, Montz B1 or Montz A3 or Kühni Rombopak, or random beds of random packings such as Dixon rings, Raschig rings, High-Flow rings or Raschig Super rings, for example.

In step a) of the method according to the invention, a material is preferably provided having the compound of the general formula II in an amount of at least 50% by weight, particularly preferably at least 70% by weight, particularly at least 90% by weight, especially at least 95% by weight, based on the total weight of the starting material. This material is then used for the reaction in step (b).

In a preferred embodiment in step a) of the method according to the invention, a material is provided having 3-methylcyclopentadecane-1,5-diol (II.1) in an amount of at least 50% by weight, particularly preferably at least 70% by weight, particularly at least 90% by weight, especially at least 95% by weight, based on the total weight of the starting material. This material is then preferably used for the reaction in step (b).

Step b):

In accordance with the invention, the starting material from step a) comprising the compound of formula (II) is subjected to a reaction in step b) at a temperature in a range from 100 to 240° C. and a pressure in a range from 1 to 150 mbar in the presence of a solvent or a solvent mixture having a vapor pressure in the range from $10^{-5}$ to 100 mbar at 180° C.

At a temperature in the range of 100 to 240° C. and a pressure in the range of 1 to 150 mbar, the conversion of 3-methylcyclopentadecane-1,5-diol (II.1) to 14-methyl-16-oxabicyclo[10.3.1]pentadecene (I.1) gives rise to the following boiling sequence (from low to high boilers): 14-methyl-16-oxabicyclo[10.3.1]pentadecene (I.1), 3-methylcyclopentadecane-1,5-dione (III.1), 3-methylcyclopentadecane-1,5-diol (II.1).

The compounds have the following vapor pressures at 180° C.:
14-methyl-16-oxabicyclo[10.3.1]pentadecene (I.1): 27 mbar
3-methylcyclopentadecane-1,5-dione (III.1): 7 mbar
3-methylcyclopentadecane-1,5-diol (II.1): 2 mbar In principle, any solvent is suitable for use in the method according to the invention which has a vapor pressure under the reaction conditions which is sufficiently below the vapor pressure of the compound of the general formula (I), especially 14-methyl-16-oxabicyclo[10.3.1]pentadecene (I.1). If the solvent forms a low-boiling azeotrope with the compound of the general formula (I), especially 14-methyl-16-oxabicyclo-[10.3.1]pentadecene (I.1), the compound (I) or (I.1) can be separated by distillation together with the solvent or solvent mixture. However, the solvent should preferably not form a high-boiling azeotrope with the compound of the general formula (I), especially 14-methyl-16-oxabicyclo[10.3.1]pentadecene (I.1), which solvent has a lower vapor pressure than the compound (II) or (II.1) at 180° C.

The boiling points of most solvents are given in standard works, such as the Handbook of Chemistry and Physics, which is published as periodic updates by CRC Press, Inc., Boca Raton, Fla., USA. In this case, the standard boiling point at 101.325 kPa is generally given. The current boiling point at the temperature and pressure which prevail under the reaction conditions may be determined by applying the Antoine equation or the Claussius-Clapeyron equation. Descriptions of these are found, for example, in the Handbook of Chemistry and Physics, 76th Edition (1995-1996), 15-19, CRC Press, Inc., Boca Raton, Fla., USA. The determination of the current boiling point of a specific solvent at the temperature and pressure which prevail under the reaction conditions also pertains to the usual knowledge of those skilled in the art.

In a first variant of the method according to the invention, a solvent is used in step b) having a vapor pressure which is lower than the vapor pressure of the compound of the general formula (II). Specifically, the method according to the invention serves to prepare 14-methyl-16-oxabicyclo[10.3.1]pentadecene (I.1) and a solvent is used in step b) having a vapor pressure which is lower than the vapor pressure of 3-methylcyclopentadecane-1,5-diol (II.1).

The vapor pressure refers in this case to the temperature which prevails under the reaction conditions in step b).

In a specific configuration of this first variant, the compound of formula (I.1) (14-methyl-16-oxabicyclo[10.3.1]pentadecene) is separated from the reaction mixture by one-stage distillation (i.e. without rectification).

In a second preferred variant of the method according to the invention, a solvent is used in step b) having a vapor pressure which is between the vapor pressure of compound (I) and compound (II). Specifically, the method according to the invention serves to prepare 14-methyl-16-oxabicyclo[10.3.1]pentadecene (I.1), and a solvent is used in step b) having a vapor pressure between the vapor pressure of 14-methyl-16-oxabicyclo[10.3.1]pentadecene (I.1) and 3-methylcyclopentadecane-1,5-diol (II.1). The vapor pressure refers in this case to the temperature which prevails under the reaction conditions in step b). In this variant, it is possible in an advantageous manner that, during the distillative separation of 14-methyl-16-oxabicyclo[10.3.1]pentadecene (I.1) in step c), the unreacted 3-methylcyclopentadecane-1,5-diol (II.1), the catalyst and the solvent largely remain in the reaction zone. The product mixture obtained in this case may still comprise 14-methyl-16-oxabicyclo[10.3.1]hexadecane (VI.1) and/or 3-methylcyclopentadecane-1,5-dione (III.1), in addition to 14-methyl-16-oxabicyclo[10.3.1]-pentadecene (I.1).

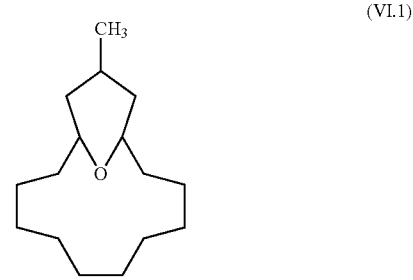
(VI.1)

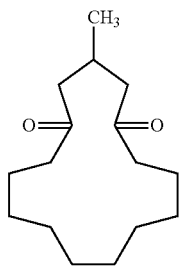

If desired, the product mixture which may still comprise 14-methyl-16-oxabicyclo-[10.3.1]hexadecane (VI.1) and/or 3-methylcyclopentadecane-1,5-dione (III.1), in addition to 14-methyl-16-oxabicyclo[10.3.1]pentadecene (I.1), may be subjected to a separation by distillation.

In a third particularly preferred variant of the method according to the invention, a solvent is used in step b) having a vapor pressure which is between the vapor pressure of compound (I) and the vapor pressure of compound (III). Specifically, the method according to the invention serves to prepare 14-methyl-16-oxabicyclo[10.3.1]pentadecene (I.1), and a solvent is used in step b) having a vapor pressure between the vapor pressure of 14-methyl-16-oxabicyclo[10.3.1]pentadecene (I.1) and 3-methylcyclopentadecane-1,5-dione (III.1). The vapor pressure refers in this case to the temperature which prevails under the reaction conditions in step b). In this variant, it is possible in an advantageous manner that, during the distillative separation of 14-methyl-16-oxabicyclo[10.3.1]pentadecene (I.1) in step c), the unreacted 3-methylcyclopentadecane-1,5-diol (II.1), the catalyst and the solvent and, if present, 3-methylcyclopentadecane-1,5-dione (III.1), largely remain in the reaction zone.

In accordance with the invention, a solvent or a solvent mixture is used in step b) having a vapor pressure in the range of $10^{-5}$ to 100 mbar at 180° C. The solvent or solvent mixture preferably has a vapor pressure in the range of $10^{-4}$ to 100 mbar, in particular $10^{-3}$ to 100 mbar, at 180° C.

The solvent used in step b) is preferably selected from
aliphatic, cycloaliphatic and aromatic hydrocarbons,
aliphatic, cycloaliphatic and aromatichen monohydric and polyhydric alcohols,
ether alcohols, polyether polyols and mono- and dialkyl ethers thereof, aromatic ethers and open-chain aliphatic ethers,
ketones,
esters,
mixtures thereof.

The solvent used in step b) is particularly preferably selected from
$C_{10}$-$C_{30}$-alkanes,
$C_{6}$-$C_{30}$-alkanols,
$C_{2}$-$C_{30}$-alkanediols,
polyalkylene glycols and mono- and dialkylethers thereof,
mixtures thereof.

If the solvent used in step b) comprises at least one $C_{10}$-$C_{30}$-alkane or consists of a $C_{10}$-$C_{30}$-alkane, this is linear or branched and is preferably selected from $C_{12}$-$C_{28}$-alkanes, particularly preferably $C_{14}$-$C_{24}$-alkanes.

Suitable $C_{10}$-$C_{30}$-alkanes are, e.g. n-decane, n-undecane, n-dodecane, n-tridecane, n-tetradecane, n-pentadecane, n-hexadecane, n-heptadecane, n-octadecane, n-nonadecane, n-eicosane, n-heneicosane, n-docosane, n-tricosane, n-tetracosane and constitutional isomers thereof.

Preference is given to using at least one linear $C_{14}$-$C_{24}$-alkane as solvent in step b).

In particular, the solvent used in step b) is selected from n-heptadecane, n-octadecane, n-nonadecane, n-eicosane, n-heneicosane and mixtures thereof.

If the solvent used in step b) comprises at least one $C_{10}$-$C_{30}$-alkanol or consists of a $C_{10}$-$C_{30}$-alkanol, the $C_{10}$-$C_{30}$-alkyl residues are linear or branched and are preferably selected from $C_{12}$-$C_{28}$-alkyl residues, particularly preferably $C_{14}$-$C_{24}$-alkyl residues.

Suitable $C_{10}$-$C_{30}$-alkyl residues are, e.g. n-decyl, n-undecyl, n-dodecyl, n-tridecyl, n-tetradecyl, n-pentadecyl, n-hexadecyl, n-heptadecyl, n-octadecyl, n-nonadecyl, n-eicosyl, n-heneicosyl, n-docosyl, n-tricosyl, n-tetracosyl and constitutional isomers thereof.

Preference is given to using at least one linear $C_{14}$-$C_{24}$-alkanol as solvent in step b).

The solvent used in step b) is particularly preferably selected from 1-tetradecanol (myristyl alcohol), 1-pentadecanol, 1-hexadecanol (cetyl alcohol or palmityl alcohol), 1-heptadecanol (margaryl alcohol), 1-octadecanol (stearyl alcohol), isostearyl alcohol, 1-eicosanol (arachidyl alcohol), 1-docosanol (behenyl alcohol), 1-teracosanol (lignoceryl alcohol) and mixtures thereof.

In particular, the solvent used in step b) is selected from 1-pentadecanol, 1-hexadecanol, 1-heptadecanol, 1-octadecanol and mixtures thereof.

Furthermore, the solvent used in step b) preferably comprises at least one polyether polyol or a monoalkyl ether or a dialkyl ether thereof.

Suitable polyether polyols and the mono- and di($C_{1}$-$C_{6}$-alkyl ethers) thereof may be linear or branched, preferably linear. Suitable polyetherols and the mono- and di($C_{1}$-$C_{6}$-alkyl ethers) thereof generally have a number-average molecular weight in the range of about 200 to 2000, preferably 280 to 1000. Preferred polyetherols are polyalkylene glycols, such as polyethylene glycols, polypropylene glycols, polytetrahydrofurans and alkylene oxide copolymers. Suitable alkylene oxides for preparation of alkylene oxide copolymers are, for example, ethylene oxide, propylene oxide, epichlorohydrin, 1,2- and 2,3-butylene oxide. Suitable examples are copolymers of ethylene oxide and propylene oxide, copolymers of ethylene oxide and butylene oxide, and copolymers of ethylene oxide, propylene oxide and at least one butylene oxide. The alkylene oxide copolymers may comprise the copolymerized alkylene oxide units in random distribution or in the form of blocks. Particularly preferred polyether components are ethylene oxide homopolymers.

Suitable polyether components PE) are additionally the mono- and di($C_{1}$-$C_{2}$-alkyl ethers) of the above-described polyetherols. Preference is given to polyalkylene glycol monomethyl ethers and polyalkylene glycol dimethyl ethers.

Suitable polyalkylene glycols are the polyethylene glycols obtainable from BASF SE under the brand Lutrol E®. Particularly suitable is Lutrol E® 400 having an average of 8 ethylene oxide repeating units.

The solvent content of the reaction mixture in step b) is preferably always maintained at at least 20% by weight, preferably at least 30% by weight, in particular at least 50% by weight, based on the total weight of the reaction mixture in the reaction zone.

The amount of catalyst in the reaction zone is preferably 0.001 to 5% by weight, particularly preferably 0.01 to 3% by weight, based on the total weight of the reaction mixture in the reaction zone.

The amount of catalyst in the reaction zone is preferably 0.1 to 15% by weight, particularly preferably 0.5 to 10% by weight, particularly 1 to 5% by weight, based on the maximum weight of the compound of the general formula (II), especially 3-methylcyclopentadecane-1,5-diol (II.1) present in the reaction zone.

The values mentioned above for the amount of catalyst in the reaction zone applies in principle to the batchwise, semi-continuous and continuous modes of operation. The catalysts used according to the invention are characterized by good service lives such that fresh cyclopentadecane-1,5-diol (II) can be introduced into the reaction zone over a long reaction time without the catalyst activity markedly declining. The method according to the invention thereby enables the preparation of compounds of the general formula (I) from cyclopentadecane-1,5-diols (II) using very low amounts of catalyst based on the total conversion.

The reactors which may be used as the reaction zone in step b) are not subject to any particular limitations. Accordingly, at least one stirred reactor, at least one tubular reactor or at least one loop reactor, for example, may be used as reactors. The reactors may be equipped with at least one internal and/or at least one external heat exchanger. It is also possible to configure at least one of these reactors such that it has at least two different zones. Such zones may, for example, differ in reaction conditions such as, for example, the temperature or the pressure and/or in the geometry of the zone such as, for example, the volume or the cross section. If the reaction is carried out in two or more reactors, two or more identical reactor types or at least two different reactor types may be used.

The cyclopentadecane-1,5-diol (II) is advantageously introduced into the reaction zone in liquid form. In a first preferred embodiment, a melt of cyclopentadecane-1,5-diol (II) is introduced into the reaction zone. In a second preferred embodiment, cyclopentadecane-1,5-diol (II) is introduced into the reaction zone as a solution in the solvent used. If the method according to the invention is carried out in batch mode, cyclopentadecane-1,5-diol (II) is preferably initially charged partially or completely in the reaction zone.

As discussed, the method according to the invention specifically serves for preparing 14-methyl-16-oxabicyclo[10.3.1]pentadecene (I.1) from 3-methylcyclopentadecane-1,5-diol (II.1). If 3-methylcyclopentadecane-1,5-diol (II.1) is fed to the reaction zone during the course of the reaction in step b), in a first preferred embodiment a melt of 3-methylcyclopentadecane-1,5-diol (II.1) is introduced into the reaction zone. This variant is suitable in batchwise, semi-continuous or continuous modes of operation. Since in this variant the high-boiling solvent used according to the invention is not additionally fed to the reaction zone, the accumulation thereof can be effectively avoided.

In a second preferred embodiment, 3-methylcyclopentadecane-1,5-diol (II.1) is fed to the reaction zone as a solution in a low-boiling solvent during the course of the reaction in step b). For this purpose, the same low-boiling solvents may be used as for the feeding of the suspension catalyst into the reaction zone. These low-boiling solvents may be removed by distillation in the first phase at the start of the reaction. Furthermore, these low-boiling solvents can be condensed at the top of the column together with the 14-methyl-16-oxabicyclo[10.3.1]pentadecene (I.1) and be discharged. Alternatively, the low-boiling solvents can also be discharged in gaseous form.

In a third embodiment, 3-methylcyclopentadecane-1,5-diol (II.1) is fed to the reaction zone as a solution in the (high-boiling) solvent used according to the invention during the course of the reaction in step b). This variant is not preferred for the continuous feeding of 3-methylcyclopentadecane-1,5-diol (II.1), since it can lead to an accumulation of the solvent in the reaction zone. A separation by distillation of this high-boiling solvent, together with 14-methyl-16-oxabicyclo[10.3.1]pentadecene (I.1), is possible in a one-stage distillation.

A heterogeneous catalyst which is capable of dehydrogenating and dehydrating cyclopentadecane-1,5-diol (II) is used for the reaction in step b).

The catalysts used in step b) preferably comprise at least one transition metal of groups 7, 8, 9, 10 and 11 of the IUPAC Periodic Table. The catalysts used in step b) more preferably comprise at least one element selected from the group consisting of Cu, Co, Rh, Ir, Ni, Pd, Pt, Re, Fe, Ru and Au. The catalysts used particularly preferably comprise Cu. In a specific embodiment, copper is the only metal used in the active mass of the catalyst.

The catalysts used in step b) comprise said transition metals, especially the transition metals mentioned as preferred, generally as such, applied to a support, as precipitation catalysts, as Raney catalysts or as mixtures thereof. Raney copper is especially used in step b).

Inert support materials used for the catalysts used in step b) may be virtually all prior art support materials as used advantageously in the preparation of supported catalysts, for example carbon, $SiO_2$ (quartz), porcelain, magnesium oxide, tin dioxide, silicon car-bide, $TiO_2$ (rutile, anatase), $Al_2O_3$ (alumina), aluminum silicate, steatite (magnesium silicate), zirconium silicate, cerium silicate or mixtures of these support materials. Preferred support materials are carbon, aluminum oxide and silicon dioxide.

If two or more metals are used, these can be present separately or as an alloy. It is possible in this case to use at least one metal as such and at least one other metal as Raney catalyst or at least one metal as such and at least one other metal applied to at least one support, or at least one metal as Raney catalyst and at least one other metal applied to at least one support, or at least one metal as such and at least one other metal as Raney catalyst and at least one other metal applied to at least one support.

The catalysts can be used in the form of shaped bodies, for example in the form of spheres, rings, cylinders, cubes, cuboids or other geometric bodies. Unsupported catalysts can be formed by customary processes, e.g. by extrusion, tabletting etc. The form of the supported catalysts is determined by the form of the support. Alternatively, the support can be subjected to a shaping process before or after the application of the catalytically active component(s). The catalysts can be used, for example, in the form of pressed cylinders, tablets, pellets, wagonwheels, rings, stars, or extrudates such as solid extrudates, polylobal extrudates, hollow extrudates and honeycombs, or other geometric bodies.

Suitable reactors for the reaction in step b) are reactors known to those skilled in the art which are suitable for reactions under simultaneous evaporation of one component and/or release of a gaseous component and/or reaction under reduced pressure. These include, for example, stirred tanks (which may also be configured as stirred tank cascades), tubular reactors, tube bundle reactors, circulation reactors, etc.

For supplying the heat required for the reaction in step b) and the separation by distillation of compound (I), especially 14-methyl-16-oxabicyclo[10.3.1]pentadecene (I.1), in step c), one or more of the reactors can be provided with at least one heating device. If a single reactor is used, this is generally provided with a heating device. If two or more reactors are used, generally at least the first reactor, especially all reactors, is/are provided with a heating device. Heat can also be supplied at least in part by heating an external circulation stream or by internal heating in at least one of the reactors. For the internal heating, it is possible to use the apparatuses customary for this purpose, generally hollow modules such as Field tubes, tube coils, heat exchanger plates, etc. Alternatively, the reaction can also be effected in a heated tube bundle reactor.

Step b) of the method according to the invention using at least one heterogeneous catalyst can be conducted in fixed bed mode or suspension mode. Operation in fixed bed mode can be conducted here, for example, in liquid phase mode or in trickle mode.

If, for example, step b) is carried out with at least one suspension catalyst, the reaction zone preferably comprises at least one stirred reactor. The heterogeneous catalysts are usually used here in a finely divided state and are in fine suspension in the reaction medium. For this purpose, the catalyst is preferably introduced into the reaction zone as a suspension in the solvent used according to the invention or a low-boiling solvent different therefrom. Suitable low-boiling solvents different from the solvents used according to the invention are preferably selected from water, $C_1$- to $C_4$-alkanols and mixtures thereof. Preference is given to water, methanol and mixtures thereof. These low-boiling solvents may be removed by distillation before or at the start of the reaction. Generally, the procedure in such cases is to initially charge the suspension catalyst in the reaction zone. This procedure is independent of whether the method according to the invention is carried out batchwise, semi-continuously or continuously. The catalysts used are characterized by a long service life. It is possible, however, in the case of declining catalyst activity, especially in the continuous process, to introduce fresh catalyst suspension into the reaction zone. In this case, the freshly introduced suspension catalyst is preferably used as a suspension in the solvent used in accordance with the invention.

Step c):

In step c) of the method according to the invention, a fraction comprising the compound of formula (I) is separated by distillation from the reaction mixture present in the reaction zone.

Specifically, the method according to the invention serves for preparing 14-methyl-16-oxabicyclo[10.3.1]pentadecene (I.1) from 3-methylcyclopentadecane-1,5-dial (II.1). Then in step c) of the method according to the invention, a fraction comprising the compound of formula (I.1) (14-methyl-16-oxabicyclo[10.3.1]pentadecene) is separated by distillation from the reaction mixture present in the reaction zone.

In particular, an apparatus is used to carry out the method according to the invention which apparatus comprises a reaction zone and a distillation zone linked thereto. In a preferred embodiment, the apparatus according to the invention used for carrying out steps b) and c) comprises a stirred tank or a stirred tank cascade, wherein the stirred tank, or in the case of a stirred tank cascade, the final stirred stank, is provided with a distillation apparatus in the direction of flow.

The reaction in step b) and also the distillative separation of a fraction comprising the compound of formula (I) (especially 14-methyl-16-oxabicyclo[10.3.1]pentadecene (I.1)) in step c) is preferably carried out at a temperature in a range of 100 to 240° C. The temperature is particularly preferably in a range of 120 to 220° C.

The reaction in step b) and also the distillative separation of a fraction comprising the compound of formula (I) (especially 14-methyl-16-oxabicyclo[10.3.1]pentadecene (I.1)) in step c) is preferably carried out at a pressure in a range of 0.1 to 100 mbar. The pressure is particularly preferably in a range of 0.5 to 50 mbar.

The first filling of the reaction zone is preferably carried out prior to the start of the reaction at a temperature in the range of 10 to 100° C., preferably 15 to 70° C. The temperature is determined here by the components of the reaction mixture used. If, for example, hexadecanol is used as solvent, the filling is carried out advantageously above the melt temperature of 49° C. If, for example, methanol is used as co-solvent for charging the catalyst suspension, the filling is carried out advantageously below the boiling temperature of ca. 67° C. The temperature during the reaction in step b) and the distillative separation in step c) can also be increased in one or more steps or continuously, for example, to accelerate the separation of the compound of the general formula (I) formed during the reaction. Furthermore, the temperature during the reaction in step b) and the distillative separation in step c) can also be reduced in one or more steps or continuously, for example, in order to feed components to the reaction zone, such as fresh cyclopentadecane-1,5-diol (II), fresh solvent or fresh catalyst and/or in order to interrupt the separation of the compound of the general formula (I), for example, in order to increase again the content of the compound of the general formula (I) in the reaction zone after a phase of separation.

The first filling of the reaction zone preferably takes place at atmospheric pressure before the start of the reaction. The pressure during the reaction in step b) and the distillative separation in step c) can also be reduced in one or more steps or continuously, for example, in order to accelerate the separation of the compound of the general formula (I) formed during the reaction. Furthermore, the pressure during the reaction in step b) and the distillative separation in step c) can also be increased in one or more steps or continuously, for example, in order to feed components to the reaction zone, such as fresh cyclopentadecane-1,5-diol (II), fresh solvent or fresh catalyst and/or in order to interrupt the separation of the compound of the general formula (I), for example, in order to increase again the content of the compound of the general formula (I) in the reaction zone after a phase of separation.

Optionally, before the start of the actual reaction, the pressure in the reaction zone and the distillation zone is initially reduced (optional phase 1). In addition, before the start of the actual reaction, the temperature in the reaction zone may already be increased. This phase 1, however, is characterized in that the temperature is below 100° C. and/or the pressure is above 100 mbar. In a preferred embodiment, the pressure is initially reduced in the phase before the start of the reaction, preferably to a value in the range of 100 to 500 mbar, particularly preferably 180 to 300 mbar. In this phase, the temperature is preferably not increased or increased at most to 50° C., compared to the temperature in the first filling of the reaction zone. In a specific embodiment, the reaction in step b) is carried out with at least one suspension catalyst, wherein the catalyst is introduced into the reaction zone in a low-boiling solvent. These low-boiling solvents are preferably removed by distillation in the first phase at the start of the reaction.

After phase 1, the pressure in the reaction zone and the distillation zone is preferably reduced in steps or continuously. Simultaneously or independently, the temperature can be increased in steps or continuously.

Optionally, the reaction in step b) comprises a phase during which the temperature in the reaction zone is in a range of 100 to 240° C. and the pressure in the reaction zone and the distillation zone is in a range of 0.1 to 150 mbar, but in which none of the fraction comprising the compound of formula (I) is separated by distillation from the reaction mixture (optional phase 2). In this phase, the compound of the general formula (I) (especially 14-methyl-16-oxabicyclo[10.3.1]pentadecene (I.1)) is formed in the reaction zone from the compound of the general formula (II) (especially 3-methylcyclopentadecane-1,5-diol (II.1)) such that the concentration of the compound of the general formula (I) (especially 14-methyl-16-oxabicyclo[10.3.1]pentadecene (I.1)) increases in the reaction mixture. Specifically, a portion of the compound of the general formula (I) (especially 14-methyl-16-oxabicyclo[10.3.1]pentadecene (I.1)) is in the distillation zone in phase 2, even if no compound of the general formula (I) (especially 14-methyl-16-oxabicyclo[10.3.1]pentadecene (I.1)) is withdrawn therefrom. By means of this procedure, the residence time of the compound of the general formula (I) (especially 14-methyl-16-oxabicyclo[10.3.1]pentadecene (I.1)) in the reaction zone can be minimised and therefore its thermal stress.

The reaction in step b) comprises a phase during which the temperature in the reaction zone is in a range of 100 to 240° C. and the pressure in the reaction zone and the distillation zone is in a range of 0.1 to 150 mbar, and in which the compound of formula (I) (especially 14-methyl-16-oxabicyclo[10.3.1]pentadecene (I.1)) is separated by distillation from the reaction mixture (phase 3).

In the simplest case of carrying out the method according to the invention in batch mode without replenishing converted cyclopentadecane-1,5-diol (II), phase 3 is performed once until the cyclopentadecane-1,5-diol (II) in the reaction zone is converted as far as possible to compound (I) and this is separated as far as possible from the reaction mixture by distillation.

In the ideal case of continuously carrying out the method according to the invention, phase 3 is performed until, despite feeding cyclopentadecane-1,5-diol (II) and optionally further components (such as solvent or catalyst) into the reaction zone, the concentration of compound (I) in the reaction zone has fallen such that an effective separation by distillation, i.e. in sufficient amount and purity, is no longer possible in a technically viable manner.

Optionally, the reaction in step b) comprises a phase (optional phase 4) in which the distillative separation of compound (I) from the reaction mixture is interrupted. Such a phase can serve the purpose, for example, of feeding components to the reaction zone, such as fresh cyclopentadecane-1,5-diol (II), fresh solvent or fresh catalyst and/or to increase again the content of compound (I) in the reaction zone after a phase of separation.

Another phase 3 can follow on from phase 4, wherein phases 3 and 4 can in principle be performed in succession as often as desired.

In the simplest case, the distillation zone (i.e., the distillation apparatus used according to the invention) consists of an apparatus for one-stage (simple) distillation. The person skilled in the art is aware of suitable apparatuses for one-stage distillation. In such an apparatus, no substance exchange between vapors and condensate essentially occur. In other words, simple distillation takes place without rectification. In this embodiment, a solvent is preferably used in step b) having a vapor pressure which is lower than the vapor pressure of cyclopentadecane-1,5-diol (II). The vapor pressure refers in this case to the temperature which prevails under the reaction conditions in step b). The solvent is then preferably selected from polyalkylene glycols and mono- and dialkyl ethers thereof. In particular, through the addition of the solvent, a better mixing of the reaction zone is ensured. Alternatively, a solvent is used having a vapor pressure which is between the vapor pressure of compound (I) and the vapor pressure of compound (II).

Specifically, the method according to the invention serves for preparing 14-methyl-16-oxabicyclo[10.3.1]pentadecene (I.1) from 3-methylcyclopentadecane-1,5-diol (II.1). Preference is then given to using a solvent having a vapor pressure which is between the vapor pressure of 14-methyl-16-oxabicyclo[10.3.1]pentadecene (I.1) and the vapor pressure of 3-methylcyclopentadecane-1,5-diol. The temperature can thereby be kept low. Furthermore, the content of compound (I) in the reaction zone can thus more easily be kept to a low level. The solvent can then subsequently be separated from compound (I), for example, by distillation.

The product separated by one-stage distillation in step c) preferably has a content of the compound of the general formula (I) of 75 to 95% by weight, based on the total weight of the product separated.

Specifically, the method according to the invention serves for preparing 14-methyl-16-oxabicyclo[10.3.1]pentadecene (I.1) from 3-methylcyclopentadecane-1,5-diol (I1.1). The product separated by one-stage distillation in step c) then preferably has a content of 14-methyl-16-oxabicyclo[10.3.1]pentadecene (I.1) of 75 to 95% by weight, based on the total weight of the product separated.

In a typical composition for preparing 14-methyl-16-oxabicyclo[10.3.1]pentadecene (I.1) from 3-methylcyclopentadecane-1,5-diol (II.1), the product separated by one-stage distillation in step c) comprises the following compounds, each based on the total weight of the product separated:
14-methyl-16-oxabicyclo[10.3.1]pentadecene (I.1): 75-95% by weight,
3-methylcyclopentadecane-1,5-diol (II.1): 0-5% by weight,
3-methylcyclopentadecane-1,5-dione (III.1): 1-10% by weight,
14-methyl-16-oxabicyclo[10.3.1]hexadecane (VI.1): 0-15% by weight.

The product separated by one-stage distillation in step c) may, if desired, be subjected to a further work-up. The product separated by one-stage distillation in step c) is preferably subjected to a further distillation to obtain at least one fraction enriched in the compound (I) (especially 14-methyl-16-oxabicyclo[10.3.1]pentadecene (I.1)) and at least one fraction depleted in compound (I) (especially 14-methyl-16-oxabicyclo-[10.3.1]pentadecene (I.1)). Suitable distillation apparatuses are those mentioned in step a) for the distillative separation of the reaction mixture from the hydrogenation of compound (III).

For the distillative separation of compound (I) (especially 14-methyl-16-oxabicyclo-[10.3.1]pentadecene (I.1)) obtained in the reaction in step b), all apparatuses for the distillative separation of reaction mixtures comprising liquid components are generally suitable. Suitable apparatuses include distillation columns such as tray columns, which may be equipped with bubble-cap trays, sieve plates, sieve trays, structured packings or random packings, spinning band columns, evaporators such as thin film evaporators, falling film evaporators, forced circulation evaporators, Sambay evaporators etc., and combinations thereof. Suitable structured packings or random packings are, e.g. sheet metal or fabric packings such as Sulzer Mellapak®, Sulzer BX, Mont B1 or Montz A3 or Kühni Rombopak, or random beds of random packings such as Dixon rings, Raschig rings, High-Flow rings or Raschig Super rings, for example.

For the distillative separation of compound (I) (especially 14-methyl-16-oxabicyclo-[10.3.1]pentadecene (I.1)) obtained in the reaction in step b), at least one distillation column is particularly preferably used. In particular, at least one distillation column having at least 10 theoretical plates is used for the distillative separation of compound (I) (especially 14-methyl-16-oxabicyclo[10.3.1]pentadecene (I.1)) obtained in the reaction in step b). The distillation column used for the distillative separation is generally in direct connection with the reaction zone, e.g. a stirred reactor. For the reaction in step b) and for the distillative separation of compound (I) (especially 14-methyl-16-oxabicyclo-[10.3.1]pentadecene (I.1)) in step c), a stirred reactor is preferably used to which a distillation column has been installed. The stirred reactor thus functions principally as heated bottom for the distillation column. In the case of the use of two or more reactors connected in series, each of these reactors may be equipped with a distillation column or the vapor containing compound (I) can be fed via one or more lines to a distillation column, preferably from the last tank of the reactor cascade in the direction of flow.

For the distillative separation of compound (I) (especially 14-methyl-16-oxabicyclo-[10.3.1]pentadecene (I.1)) obtained in the reaction in step b) using at least one distillation column, the solvent used according to the invention preferably has a vapor pressure which is between the vapor pressure of compound (I) and the vapor pressure of compound (II). The solvent used according to the invention particularly preferably has a vapor pressure which is between the vapor pressure of compound (I) and the vapor pressure of compound (III). The suitable and preferred solvents mentioned previously for use in step b) are fully incorporated by reference.

The compound (I) (especially 14-methyl-16-oxabicyclo [10.3.1]pentadecene (I.1)) released in the reaction in step b) is preferably separated from the reaction mixture in a batchwise mode or continuously.

In a specific embodiment, a compound (II) (especially 3-methylcyclopentadecane-1,5-diol (II.1)) is fed continuously to the reaction zone and the compound (I) (especially 14-methyl-16-oxabicyclo[10.3.1]pentadecene (I.1)) released is separated continuously from the reaction mixture.

The product separated by fractional distillation in step c) preferably has a content of compound (I) (especially 14-methyl-16-oxabicyclo[10.3.1]pentadecene (I.1)) of 80 to 99% by weight, particularly preferably 85 to 99% by weight, based on the total weight of the product separated.

In a typical composition for preparing 14-methyl-16-oxabicyclo[10.3.1]pentadecene (I.1) from 3-methylcyclopentadecane-1,5-diol (II.1), the product separated by fractional distillation in step c) comprises the following compounds, each based on the total weight of the product separated:
  14-methyl-16-oxabicyclo[10.3.1]pentadecene (I.1): 80-99% by weight,
  3-methylcyclopentadecane-1,5-diol (II.1): 0-5% by weight,
  3-methylcyclopentadecane-1,5-dione (III.1): 0 to 5% by weight, preferably 0 to 1% by weight,
  14-methyl-16-oxabicyclo[10.3.1]hexadecane (VI.1): 0 to 15% by weight, preferably 0 to 10% by weight,
  solvent: 0 to 5% by weight, preferably 0 to 1% by weight,
  3-methylcyclopentadecan-5-ol-1-one (VII.1): 0-5% by weight.

Other compositions of the reaction mixture can also be achieved depending on the reaction conditions selected.

In the distillative separation in step c) of compound (I) (especially 14-methyl-16-oxabicyclo[10.3.1]pentadecene (I.1)) obtained in the reaction in step b), a vapor is initially drawn off which is subsequently at least partially condensed. Condensation or partial condensation of the vapor can be effected using any suitable condensers. These can be cooled with any desired cooling media. Preference is given to condensers with air-cooling and/or water-cooling. The condenser is located generally at the top, i.e. at the upper end of the distillation column or is integrated with the head of the column.

In the context of the present invention, the terms "top of the column" or "column head" are understood to mean the region of a distillation column which is located at the upper end, i.e. generally the upper fifth, preferably the upper tenth, of the distillation column.

Generally, the ratio of stream removed to the stream recirculated into the column is in the range from 1:1 to 1:30, and especially in the range of 1:1 to 1:20.

Typically, the separation of compound (1) (especially 14-methyl-16-oxabicyclo[10.3.1]-pentadecene (I.1)) obtained in the reaction in step b) is initiated as soon as the temperature at the column head no longer essentially changes after the start of the reaction in step b). This is the case, for example, after a few minutes up to a few hours.

During the distillative separation of compound (I) (especially 14-methyl-16-oxabicyclo-[10.3.1]pentadecene (I.1)) obtained in the reaction in step b), the reflux ratio, as defined above, is preferably adjusted so that the temperature at the column head remains constant as far as possible. The expression "constant as far as possible" in this context signifies that the temperature at the column head fluctuates by less than 10° C., for example, less than 5° C. or 3° C. In other words, the reflux ratio at the column head is adjusted so that the composition (purity) of the top stream with respect to compound (I) (especially 14-methyl-16-oxabicyclo[10.3.1]pentadecene (I.1)) remains essentially constant.

In a preferred embodiment of the method according to the invention, at least one compound (II) (especially 3-methylcyclopentadecane-1,5-diol (II.1)) is in addition fed to the reaction in step b). The at least one compound (11) for the reaction in step b) can be fed in steps or continuously, preferably continuously over the entire course of the reaction. By means of the feeding, the loss of compound (II) in the reaction mixture caused by the distillative discharge of compound (I) (especially 14-methyl-16-oxabicyclo[10.3.1]-pentadecene (I.1)) should be compensated. The at least one compound (II) is preferably fed in such a manner that the amount of compound (II) in the reaction mixture during the distillative discharge of compound (I) (especially 14-methyl-16-oxabicyclo-[10.3.1]pentadecene (I.1)) remains constant as far as possible.

Step d):

In a specific embodiment of the method according to the invention, the compounds of the general formula (I) are subjected to a further reaction to obtain at least one compound of the general formula (IV)

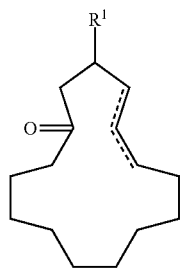

(IV)

where the symbol ══ is in one case a single bond and in one case a double bond and R¹ is hydrogen or $C_1$-$C_4$-alkyl.

In a specific embodiment, R¹ is methyl.

Step d):

In a further specific embodiment of the method according to the invention, the compounds of the general formula (IV) are subjected to a further reaction to obtain at least one compound of the general formula (V)

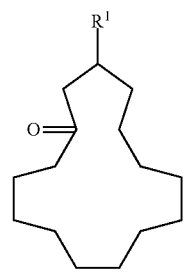

(V)

where R¹ is hydrogen or $C_1$-$C_4$-alkyl.

In a specific embodiment, R¹ is methyl.

DESCRIPTION OF FIGURES

FIG. 1 shows an apparatus which is in principle suitable for continuous, semi-continuous (semi-batch) or discontinuous (batch) modes of carrying out the method according to the invention. 3-Methylcyclopentadecane-1,5-diol is introduced into reactor R and is reacted in the presence of a heterogeneous catalyst. In the discontinuous mode of operation, 3-methylcyclopentadecane-1,5-diol is added prior to the start of the reaction. Optionally, after decline of the content of 3-methylcyclopentadecane-1,5-diol in reactor R below a certain threshold, fresh 3-methylcyclopentadecane-1,5-diol can be introduced into reactor R. This can be carried out both once and repeatedly. In the continuous mode of operation, 3-methylcyclopentadecane-1,5-diol is added depending on its consumption for preparing 14-methyl-16-oxabicyclo[10.3.1]pentadecene. The 14-methyl-16-oxabicyclo[10.3.1]pentadecene formed in reactor R is separated by distillation via column K and is condensed in a condenser linked with the heat exchanger W. A semi-continuous mode of operation is also possible, in which one of the steps, addition of 3-methylcyclopentadecane-1,5-diol or the separation of 14-methyl-16-oxabicyclo[10.3.1]pentadecene, is carried out continuously and the other in batch mode.

The examples which follow serve to illustrate the invention, but without restricting it in any way.

EXAMPLES

List of Compounds:
14-methyl-16-oxabicyclo[10.3.1]pentadecene (I.1),
3-methylcyclopentadecane-1,5-diol (II.1),
3-methylcyclopentadecane-1,5-dione (III.1),
14-methyl-16-oxabicyclo[10.3.1]hexadecane (VI.1),
3-methylcyclopentadecan-5-ol-1-one (VII.1).

Gas chromatographic analyses were carried out in accordance with the following method:
GC system: Agilent 7890 Series A
Column: DB WAX 30 m (length)×0.32 mm (internal diameter);
FD 0.25 µm (film);
Injector temperature: 230° C.; detector temperature 280° C.; flow rate: 1.5 ml
Temperature program: Starting temp.: 80° C. to 250° C. at 3° C./min, 250° C., 15 minutes isothermal.

The compounds present in the samples measured may have different isomers, for example, with respect to the position of the substituents on the ring system (cis,trans-isomers) and the position of the substituents on the double bonds. Insofar as these isomers have different retention times, the sum total of all determinable area integrals was generated for determining the amount of the compound concerned. The retention times are specified below.

Example 1

(Comparative, Reaction without Added Solvent)

4.0 g of catalyst suspension (Raney copper, 30% in water) were initially charged in a 100 ml three-necked flask with 15.08 g of 3-methylcyclopentadecane-1,5-dial (II.1) (84.7 area % by GC). The pressure was initially reduced to 220 mbar at room temperature. The reaction mixture was then heated from room temperature to 166° C. and at the same time the pressure was reduced from 220 mbar to 40 mbar, whereupon the majority of the water of the catalyst suspension and also of the methanol distilled. After in-creasing the temperature to 172 to 176° C. and reducing the pressure to 1 to 2 mbar, the mixture was stirred for a further 5 h. The temperature was then increased to 180° C. and distillate was removed in one stage (without rectification) over 12 h. The head temperature was 165° C. at the start of the distillate collection and increased in the course of the distillation to 175° C. In total, 10 g of distillate were obtained. The content of 14-methyl-16-oxabicyclo[10.3.1]pentadecene (I.1) in the distillate was 10.6%, that of 3-methylcyclopentadecane-1,5-dione (III.1) was 27.7% and that of 3-methylcyclopentadecane-1,5-diol (II.1) was 8.3%. This corresponds to a yield of 9%.

Example 2

(Inventive)

3 g of catalyst suspension (Raney copper, 50% in water) were washed three times with methanol. 10 g of 3-methylcyclopentadecane-1,5-diol (II.1) (82.5% by weight by GC) in 20 g of polyethylene glycol (ca. 8 PEG units, Lutrol® E400 from BASF SE, vapor pressure at 180° C.: 0.02 mbar) were then initially charged at room temperature in a 100 ml three-necked flask together with the washed catalyst. The methanol and the residual water were distilled off slowly at 50° C. at a pressure of 250 to 3 mbar. The reaction mixture was then heated to 200° C. at a pressure of 20 mbar. The temperature was maintained for 16 hours. The pressure was then decreased to 1 mbar and the low-boiling components distilled off in one stage. Good mixing was ensured throughout the entire experiment by means of a magnetic stirrer. 4.5 g of distillate with a 14-methyl-16-oxabicyclo[10.3.1]pentadecene content of 87.2 area % by GC could be obtained, which corresponds to a yield of 52%. The 3-methylcyclopentadecane-1,5-diol content was 0.8 area % by GC and the 3-methylcyclopentadecane-1,5-dione content was 3.9 area % by GC.

Example 3

(Inventive, Reaction Mixture Diluted with High-Boiling Solvent, which Boils Between 14-methyl-16-oxabicyclo[10.3.1]pentadecene and 3-methylcyclopentadecane-1,5-dione)

0.25 g of catalyst suspension (active Raney copper, 50% in water) were washed three times with methanol. 5 g of 3-methylcyclopentadecane-1,5-diol (II.1) (82.7 area % by GC) in 10 g of 1-hexadecanol (vapor pressure at 180° C.: 11 mbar) were then initially charged at room temperature in a 100 ml three-necked flask together with the washed catalyst. Good mixing was ensured throughout the entire experiment by means of a magnetic stirrer. The temperature was initially raised to 70° C. in order to melt the 1-hexadecanol. The methanol and the residual water were distilled off slowly at 70° C. The reaction mixture was then heated to 180° C. at a pressure of 40 mbar with constant stirring. The temperature was maintained for 20 hours. A sample was taken each time at 1, 3, 5 and 20 h and analyzed by GC. In Table 1 below, the contents of the 14-methyl-16-oxabicyclo[10.3.1]pentadecene (I.1) product of the 3-methylcyclopentadecane-1,5-diol (II.1) used and also of the compounds (III.1), (VI.1) and (VII.1) are given as area % by GC (GC area %) (without consideration of the 1-hexadecanol) as a function of the reaction time.

TABLE 1

| Retention time [t/min] | 22.75/22.95 (I.1) [GC area %] | 20.7/27 (VI.1) [GC area %] | 40.5 (III.1) [GC area %] | 43.5/44.8 (VII.1) [GC area %] | 50.8-52 (II.1) [GC area %] |
|---|---|---|---|---|---|
| Reactant (0 h) | 0.0 | 0.0 | 0.0 | 0 | 98.6 |
| 1 h | 10.2 | 1.3 | 1.3 | 7.2 | 73.5 |
| 3 h | 52.2 | 5.6 | 7.3 | 13.18 | 17.3 |
| 5 h | 63.2 | 8.5 | 8.0 | 8.28 | 6.5 |
| 20 h | 66.2 | 19.6 | 7.1 | 0 | 1.1 |

The pressure was then reduced to 1 mbar and the bottom temperature to 124 to 140° C. (see Table) and the low-boiling components could be distilled off in one stage. Three distillate fractions could be drawn off (Fr1: 0.6 g, Fr2: 1.3 g, Fr3: 7.3 g). All three fractions were solid and white.

TABLE 2

| Distillate | Bottom temp. ° C. | Head temp. ° C. | Pressure mbar | (I.1) [GC area %] | (VI.1) [GC area %] | 1-Hexa-decanol [GC area %] | (III.1) [GC area %] | (II.1) [GC area %] |
|---|---|---|---|---|---|---|---|---|
| Fr1 | 124-127 | 111-114 | 1 | 62.25 | 4.7 | 22.88 | 0.87 | 1.03 |
| Fr2 | 127-129 | 112-116 | 1 | 59.4 | 5.33 | 26.22 | 1.03 | 0 |
| Fr3 | 128-140 | 116-128 | 1 | 15.79 | 4.16 | 75.76 | 2.73 | 0.34 |

Example 3 was repeated using nonadecane (vapor pressure at 180° C.: 11 mbar), tetradecanol (vapor pressure at 180° C.: 34 mbar), heptadecanol (vapor pressure at 180° C.: 7 mbar) and octadecanol (vapor pressure at 180° C.: 4 mbar) as solvent. In each case, product fractions with high 14-methyl-16-oxabicyclo[10.3.1]pentadecene content could be isolated.

Example 4

(Inventive, Reaction Mixture Diluted with Hexadecanol, which Boils Between 14-methyl-16-oxabicyclo[10.3.1]pentadecene (I.1) and 3-methylcyclopentadecane-1,5-dione (III.1), 14-methyl-16-oxabicyclo[10.3.1]pentadecene was Distilled Off in Stages Together with Hexadecanol, 3-methylcyclopentadecane-1,5-diol (II.1) was Replaced with Hexadecanol)

0.5 g of catalyst suspension (active Raney copper, 50% in water) were washed three times with methanol. 10 g of 3-methylcyclopentadecane-1,5-diol (II.1) (85.1 area % by GC) in 20 g of 1-hexadecanol (vapor pressure at 180° C.: 11 mbar) were then initially charged at room temperature in a 100 ml three-necked flask together with the washed catalyst. The temperature was initially raised to 70° C. in order to melt the 1-hexadecanol. The methanol and the residual water were distilled off slowly at 70° C. The reaction mixture was then heated to 180° C. at a pressure of 40 mbar. The temperature was maintained for 2 h. The temperature was then decreased to 145° C. and the pressure to 3 mbar and 7 g (Fraction 1) was distilled off in one stage. The distillate was analyzed and, based on the 14-methyl-16-oxabicyclo[10.3.1]pentadecene (I.1) drawn off, 3-methylcyclopentadecane-1,5-diol (II.1), together with 1-hexadecanol, was fed to the reactor so that a 3-methylcyclopentadecane-1,5-diol/1-hexadecanol ratio resulted as in the starting reaction mixture. The temperature was then increased again to 180° C. and the pressure to 40 mbar and maintained for 2 h. The pressure and the temperature were then decreased again to the values mentioned above and 4.5 g (fraction 2) and 4.8 g (fraction 3) were distilled. 3-Methylcyclopentadecane-1,5-diol (0.1) and 1-hexadecanol were again fed to the reactor. Using the same procedure as described above, a fourth fraction (fraction 4) of 10.8 g was generated. After the distillation of fraction 4, without further addition of 3-methylcyclopentadecane-1,5-diol and 1-hexadecanol, the reaction mixture was maintained at 180° C. and 40 mbar for a further 24 h and finally 5.1 g of distillate (fraction 5) were distilled off.

1,5-dione could not be detected in any of the fractions. The main by-product in the distillate was ether.

TABLE 3

|  | (I.1)<br>[GC area<br>%] | (VI.1)<br>[GC area<br>%] | 1-<br>Hexa-<br>decanol<br>[GC area<br>%] | (III.1)<br>[GC area %] | (VII.1)<br>[GC area<br>%] | (II.1)<br>[GCarea<br>%] |
|---|---|---|---|---|---|---|
| Retention time | 22.5/22.6 | 26.7 | 34.1 | 40.1 | 43.2/44.5 | 50.8-52 |
| a) | 0.0 | 0.0 | 0.0 | 0.0 | 0.0 | 95.3 |
| b) | 22.46 | 2.89 | not integrated | 9.68 | 25.59 | 28.12 |
| c) | 20.1 | 1.6 | 70.2 | 1.9 | 2.92 | 3.1 |
| d) | 15.1 | 4.7 | not integrated | 12.2 | 28.03 | 27.5 |
| e) | 12.3 | 3.0 | not integrated | 8.2 | 15.74 | 43.9 |
| f) | 39.4 | 4.3 | 42.5 | 1.5 | 0.8 | 1.4 |
| g) | 10.8 | 3.7 | 79.8 | 2.3 | 1.22 | 0.3 |
| h) | 11.2 | 4.4 | not integrated | 10.9 | 14.37 | 51.3 |
| i) | 5.9 | 2.5 | not integrated | 6.4 | 8.07 | 68.8 |
| k) | 10.6 | 3.0 | 81.9 | 1.2 | 0.36 | 2.7 |
| l) | 5.4 | 2.4 | not integrated | 5.3 | 3 | 79.2 |
| m) | 47.1 | 3.1 | 48.4 | 0.0 | 0 | 0.5 |
| n) | 40.7 | 14.1 | not integrated | 13.6 | 0 | 18.2 | a) reactant (t = 0)
b) bottoms prior to draw-off of fraction 1
c) fraction 1
b) bottoms after draw-off of fraction 1
e) bottoms after addition of 3-methylcyclopentadecane-1,5-dione (II.1)/1-hexadecanol
f) fraction 2
g) fraction 3
h) bottoms after draw-off of fraction 3
i) bottoms after addition of 3-methylcyclopentadecane-1,5-dione (II.1)/1-hexadecanol
k) fraction 4
l) bottoms after draw-off of fraction 4
m) fraction 5
n) bottoms after draw-off of fraction 5

Example 5

(Inventive, Reaction Mixture Diluted with Solvent which Boils Between 14-methyl-16-oxabicyclo[10.3.1]pentadecene (II.1) and 3-methylcyclopentadecane-1,5-dione (III.1) and Also Draw-Off of 14-methyl-16-oxabicyclo[10.3.1]pentadecene (I.1) Via a Column)

1.5 g of catalyst suspension (active Raney copper, 50% in water) were washed three times with methanol. 30 g of 3-methylcyclopentadecane-1,5-diol (II.1) (95.2 area % by GC) in 60 g of 1-hexadecanol (vapor pressure at 180° C.: 11 mbar) were then initially charged at room temperature in a 100 ml three-necked flask together with the washed catalyst. A structured packing column was placed on the flask (structured packing bed height 53 cm, structured packing 3 mm Raschig rings, column internal diameter: 1.5 cm). The temperature was initially raised to 70° C. in order to melt the 1-hexadecanol. The methanol and the residual water were distilled off slowly at 70° C. The reaction mixture was then heated to 181° C. at 3 mbar top pressure with mixing by a magnetic stirrer. After 1 h, a distillate flow is set, wherein the distillate was initially collected at the top of the column under total reflux at 2 to 3 mbar top pressure. Over the next 2.5 h, a total of 10.6 g of distillate (fraction 1, Fr1) were taken off. Under constant conditions, further fractions were each taken after a further 3 h and 6 h (fraction 2, Fr2: 10.0 g, fraction 3, Fr3: 3.9 g). The hexadecanol content of all fractions was below 0.5%. The 14-methyl-16-oxabicyclo[10.3.1]pentadecene (I.1) content was 92% in fraction 1, 87% in fraction 2 and 57.8% in fraction 3. In total, this corresponds to a yield of 80%. 3-Methylcyclopentadecane-

TABLE 4

|  | (I.1)<br>[GC area %] | (VI.1)<br>[GC area %] | H-Hexadecanol<br>[GC area %] |
|---|---|---|---|
| Retention time | 22.7/22.9 | 20.6 | 33.8 |
| Fraction 1 | 92 | 2.6 | 0.4 |
| Fraction 2 | 87 | 9.8 | 0.3 |
| Fraction 3 | 57.8 | 42.3 | 0.4 |

Example 6

(Inventive, Reaction Mixture Diluted with Solvent which Boils Between 14-methyl-16-oxabicyclo[10.3.1]pentadecene (I.1) and 3-methylcyclopentadecane-1,5-dione (III.1), Continuous Reaction Procedure with Feeding of and Also Continuous Draw-Off of 14-methyl-16-oxabicyclo[10.3.1]pentadecene (I.1) Via a Column)

2.25 g of catalyst (active Raney copper, distributed in water, withdrawal from fixed bed) were washed three times with methanol. 90 g of 3-methylcyclopentadecane-1,5-diol (II.1) (97.1% by weight by GC) in 180 g of 1-hexadecanol (vapor pressure at 180° C.: 11 mbar) were then initially charged at room temperature in a 500 ml three-necked flask together with the washed catalyst. A column with structured packings was placed on the flask (packing height 60 cm, structured packing Montz DN30 A3-1000). The temperature was initially raised to 70° C. in order to melt the 1-hexadecanol. The methanol and the residual water were distilled off slowly at 70° C. The reaction mixture was then heated to 180° C. at 3 mbar top pressure with mixing by a magnetic stirrer. After 1.5 h, a distillate flow is set, wherein the distillate was initially collected at the top of the column for 1 h under total reflux at 3 mbar top pressure.

Over the following days at a total experimental time of 156 h, at an average reflux ratio of 30, a total of 17 distillate fractions were taken off. The reflux ratio in this case was varied between 15 and 40 so that the top temperature remained constant at 134° C. It was ensured by means of varying the reflux ratio that no more product was removed from the reaction mixture than was formed by the reaction. The fractions and their composition can be taken from Table 1. By means of the continuous withdrawal of 14-methyl-16-oxabicyclo[10.3.1]pentadecene (I.1), the bottom temperature was also kept constant at 180° C. Therefore, the system is not depleted of 3-methylcyclopentadecane-1,5-dial (II.1), and as many equivalents of 3-methylcyclopentadecane-1,5-diol (II.1) were replaced as were drawn off of 14-methyl-16-oxabicyclo[10.3.1]pentadecene (I.1) and by-products. The addition of 3-methylcyclopentadecane-1,5-dial (II.1) was pulsed (portionwise). As the amount of distillate taken off was slowly diminished, a further 2.25 g of catalyst were added to the reactor after 24 and 89 hours in each case. The concentrations established in the reactor can be taken from Table 2. After 104 h, no further 3-methylcyclopentadecane-1,5-diol (II.1) was replaced and the residual 3-methylcyclopentadecane-1,5-diol (II.1) was converted to 14-methyl-16-oxabicyclo-[10.3.1]pentadecene (I.1). Over the whole experiment, a yield of 80% of 14-methyl-16-oxabicyclo[10.3.1]pentadecene (I.1) was apparent, based on 3-methylcyclopentadecane-1,5-diol (II.1). In total, 383 g of starting material having a 3-methylcyclopentadecane-1,5-diol content of 93.7% were fed.

TABLE 5

Overview of the fractions. All concentration data are area % by GC.

| Fraction | Time [h] | Amount [g] | (I.1) [GC area %] Retention time 25.28 | (VI.1) [GC area %] Retention time 29.18 |
|---|---|---|---|---|
| 1 | 10.8 | 35.9 | 90.7 | 4.3 |
| 2 | 24.5 | 13.3 | 83.2 | 8.1 |
| 3 | 32.0 | 24.2 | 58.9 | 30.9 |
| 4 | 38.0 | 20.9 | 66.4 | 24.1 |
| 5 | 45.5 | 25.4 | 54.0 | 35.8 |
| 6 | 53.5 | 7.8 | 88.3 | 2.7 |
| 7 | 60.5 | 15.5 | 93.1 | 1.3 |
| 8 | 68.5 | 22.2 | 94.4 | 1.2 |
| 9 | 75.2 | 17.9 | 92.0 | 2.0 |
| 10 | 81.8 | 12.9 | 93.3 | 1.6 |
| 11 | 97.0 | 35.4 | 96.0 | 0.5 |
| 12 | 104.3 | 22.1 | 95.4 | 0.6 |
| 13[a] | 143.2 | 62.4 | 86.0 | 5.1 |

[a] = no further 3-methylcyclopentadecane-1,5-diol (II.1) replaced

TABLE 6

Overview of concentrations in the reactor. All data are area % by GC.

| Sample | Time [h] | (I.1) [GC area %] Retention time 25.28 | (VI.1) [GC area %] Retention time 29.18 | (III.1) [GC area %] Retention time 42.76 | (II.1) [GC area %] Retention time 53.55 | 1-Hexadecanol [GC area %] Retention time 36.18 |
|---|---|---|---|---|---|---|
| 1 | 10.8 | 0.3 | 1.9 | 1.1 | 28.8 | 66.5 |
| 2 | 24.5 | 0.2 | 3.1 | 1.5 | 13.9 | 79.0 |
| 3 | 32.0 | 0.0 | 2.3 | 1.3 | 30.5 | 63.5 |
| 4 | 38.0 | 0.1 | 1.4 | 1.4 | 26.4 | 66.2 |
| 5 | 53.5 | 1.8 | 3.1 | 1.3 | 35.1 | 52.4 |
| 6 | 75.2 | 1.3 | 3.1 | 1.6 | 30.7 | 54.2 |
| 7 | 89.0 | 7.9 | 1.7 | 1.6 | 29.0 | 48.3 |

TABLE 6-continued

Overview of concentrations in the reactor. All data are area % by GC.

| Sample | Time [h] | (I.1) [GC area %] Retention time 25.28 | (VI.1) [GC area %] Retention time 29.18 | (III.1) [GC area %] Retention time 42.76 | (II.1) [GC area %] Retention time 53.55 | 1-Hexadecanol [GC area %] Retention time 36.18 |
|---|---|---|---|---|---|---|
| 8 | 130.2 | 3.4 | 4.7 | 2.8 | 17.2 | 53.5 |
| 9 | 155.7 | 0.0 | 5.2 | 5.3 | 1.4 | 50.2 |

The invention claimed is:

1. A method for preparing compounds of the general formula (I)

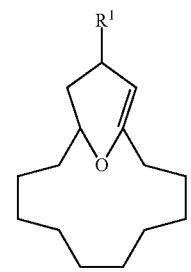

(I)

where $R^1$ is hydrogen or $C_1$-$C_4$-alkyl,
wherein the method comprises:
  a) Providing a starting material comprising a compound of the general formula (II)

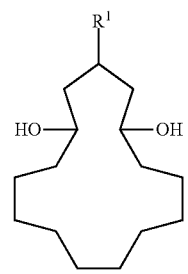

(II)

b) Subjecting the starting material provided in step a) in a reaction zone to a reaction at a temperature in a range from 100 to 240° C. and a pressure in a range from 0.1 to 150 mbar in the presence of a heterogeneous catalyst and a solvent or a solvent mixture having a vapor pressure in the range from $10^{-5}$ to 100 mbar at 180° C., and
  c) Separating the compound of formula (I) from the reaction mixture by distillation.

2. The method according to claim 1, wherein $R^1$ is hydrogen or methyl.

3. The method according to claim 1, wherein $R^1$ is methyl.

4. The method according to claim 1, wherein the reaction in step b) comprises a first phase, during which the fraction not comprising any of the compound of formula (I) is separated from the reaction mixture by distillation.

5. The method according to claim 1, wherein the vapor pressure of the solvent used in step b) is less than the vapor pressure of diol (II).

6. The method according to claim 1, wherein the vapor pressure of the solvent used in step b) is between the vapor pressure of compound (I) and the vapor pressure of compound (II).

7. The method according to claim 1, wherein the vapor pressure of the solvent used in step b) is between the vapor pressure of compound (I) and the vapor pressure of compound (III)

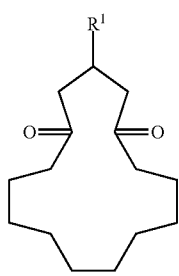

(III)

where $R^1$ is hydrogen or $C_1$-$C_4$-alkyl.

8. The method according to claim 1, wherein the solvent used in step b) is selected from the group consisting of
aliphatic, cycloaliphatic and aromatic hydrocarbons,
aliphatic, cycloaliphatic and aromatic monohydric and polyhydric alcohols,
ether alcohols, polyether polyols and mono- and dialkyl ethers thereof, aromatic ethers and open-chain aliphatic ethers,
ketones,
esters, and
mixtures thereof.

9. The method according to claim 1, wherein the solvent used in step b) is selected from the group consisting of
$C_{10}$-$C_{30}$-alkanes,
$C_6$-$C_{30}$-alkanols,
$C_2$-$C_{30}$-alkanediols,
polyalkylene glycols and mono- and dialkylethers thereof, and
mixtures thereof.

10. The method according to claim 1, wherein the compound of formula (I.1)

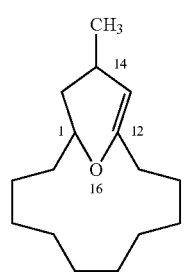 [SMILES: CC1C=C2CCCCCCCCCCC(C1)O2]

is separated from the reaction mixture in step c) by one-stage distillation and the product separated comprises the following compounds, based in each case on the total weight of the separated product:
14-methyl-16-oxabicyclo[10.3.1]pentadecene (I.1): 75-95% by weight,
3-methylcyclopentadecane-1,5-diol (II.1): 0-5% by weight,
3-methylcyclopentadecane-1,5-dione (III.1): 1-10% by weight,
14-methyl-16-oxabicyclo[10.3.1]hexadecane (VI.1): 0-15% by weight.

11. The method according to claim 1, wherein the separation in step c) comprises a fractional distillation.

12. The method according to claim 11, wherein at least one distillation column having at least 10 theoretical plates is used for the separation by distillation of a fraction comprising the compound of formula (I) in step c).

13. The method according to claim 11 for preparing 14-methyl-16-oxabicyclo[10.3.1]pentadecene (I.1), wherein the compound of formula (I) is separated from the reaction mixture in step c) by fractional distillation and the product separated comprises the following compounds, based in each case on the total weight of the separated product:
14-methyl-16-oxabicyclo[10.3.1]pentadecene (I.1): 80-99% by weight,
3-methylcyclopentadecane-1,5-diol (II.1): 0-5% by weight,
3-methylcyclopentadecane-1,5-dione (III.1): 0 to 5% by weight,
14-methyl-16-oxabicyclo[10.3.1]hexadecane (VI.1): 0 to 15% by weight,
solvent: 0 to 5% by weight, and
3-methylcyclopentadecan-5-ol-1-one (VII.1): 0-5% by weight.

14. The method according to claim 11 for preparing 14-methyl-16-oxabicyclo[10.3.1]pentadecene (I.1), wherein the compound of formula (I) is separated from the reaction mixture in step c) by fractional distillation and the product separated comprises the following compounds, based in each case on the total weight of the separated product:
14-methyl-16-oxabicyclo[10.3.1]pentadecene (I.1): 80-99% by weight,
3-methylcyclopentadecane-1,5-diol (II.1): 0-5% by weight,
3-methylcyclopentadecane-1,5-dione (III.1): preferably 0 to 1% by weight,
14-methyl-16-oxabicyclo[10.3.1]hexadecane (VI.1): 0 to 10% by weight,
solvent: 0 to 1% by weight, and
3-methylcyclopentadecan-5-ol-1-one (VII.1): 0-5% by weight.

15. The method according to claim 1, wherein the solvent content of the reaction mixture in step b) is always maintained at least 20% by weight, based on the total weight of the reaction mixture in the reaction zone.

16. The method according to claim 1, wherein the solvent content of the reaction mixture in step b) is always maintained at least 30% by weight, based on the total weight of the reaction mixture in the reaction zone.

17. The method according to claim 1, wherein the solvent content of the reaction mixture in step b) is always maintained at least 50% by weight, based on the total weight of the reaction mixture in the reaction zone.

18. The method according to claim 1, wherein the method further comprises
d) Subjecting the compounds of the general formula (I) to a reaction to obtain at least one compound of the general formula (IV)

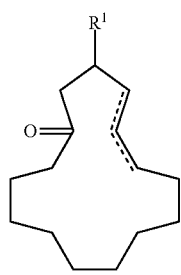
(IV)
where the symbol ⚌ is in one case a single bond and in one case a double bond and $R^1$ is hydrogen or $C_1$-$C_4$-alkyl.
19. The method according to claim 18, wherein the method further comprises
e) Subjecting the compounds of the general formula (IV) to a hydrogenation to obtain the compound of the general formula (V)
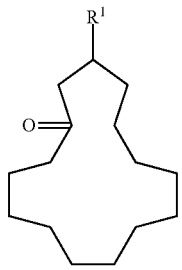
(V)
where $R^1$ is hydrogen or $C_1$-$C_4$-alkyl.
* * * * *